United States Patent
Chaggares et al.

(10) Patent No.: US 10,478,859 B2
(45) Date of Patent: *Nov. 19, 2019

(54) HIGH FREQUENCY ULTRASONIC TRANSDUCER AND MATCHING LAYER COMPRISING CYANOACRYLATE

(71) Applicant: FUIJIFILM SonoSite, Inc., Bothell, WA (US)

(72) Inventors: Nicholas Christopher Chaggares, Whitby (CA); James Mehi, Thornhill (CA); Desmond Hirson, Thornhill (CA)

(73) Assignee: FUJIFILM SonoSite, Inc., Bothell, WA (US)

( * ) Notice: Subject to any disclaimer, the term of this patent is extended or adjusted under 35 U.S.C. 154(b) by 450 days.

This patent is subject to a terminal disclaimer.

(21) Appl. No.: 15/345,479

(22) Filed: Nov. 7, 2016

(65) Prior Publication Data

US 2017/0144195 A1 May 25, 2017

Related U.S. Application Data

(60) Continuation of application No. 14/493,242, filed on Sep. 22, 2014, now Pat. No. 9,520,119, which is a
(Continued)

(51) Int. Cl.
*B06B 3/00* (2006.01)
*H01L 41/08* (2006.01)
(Continued)

(52) U.S. Cl.
CPC .............. *B06B 3/00* (2013.01); *B06B 1/06* (2013.01); *B06B 1/067* (2013.01); *B32B 7/12* (2013.01);
(Continued)

(58) Field of Classification Search
CPC ....... B06B 1/0622; B06B 1/067; G10K 11/02; G10K 11/002
See application file for complete search history.

(56) References Cited

U.S. PATENT DOCUMENTS 4,240,090 A 12/1980 Hughes et al.
4,387,720 A 6/1983 Miller et al.
(Continued)

FOREIGN PATENT DOCUMENTS

CN 1650794 A 8/2005
CN 101247754 A 8/2008
(Continued)

OTHER PUBLICATIONS

Taiwan Intellectual Property Office, Examination Opinion, TW Patent Application 104107859, dated May 7, 2018, 18 pages (with English translation).
(Continued)

*Primary Examiner* — J. San Martin
(74) *Attorney, Agent, or Firm* — Baker Botts L.L.P.

(57) ABSTRACT

In one aspect, matching layers for an ultrasonic transducer stack having a matching layer comprising a matrix material loaded with a plurality of micron-sized and nano-sized particles. In another aspect, the matrix material is loaded with a plurality of heavy and light particles. In another aspect, an ultrasound transducer stack comprises a piezoelectric layer and at least one matching layer. In one aspect, the matching layer comprises a composite material comprising a matrix material loaded with a plurality of micron-sized and nano-sized particles. In a further aspect, the composite material can also comprise a matrix material loaded with a plurality of heavy and light particles. In a further aspect, a matching layer can also comprise cyanoacrylate.

14 Claims, 7 Drawing Sheets

Related U.S. Application Data division of application No. 13/730,337, filed on Dec. 28, 2012, now Pat. No. 8,847,467, which is a continuation of application No. 12/830,904, filed on Jul. 6, 2010, now Pat. No. 8,343,289, which is a division of application No. 11/366,953, filed on Mar. 2, 2006, now Pat. No. 7,750,536.

(51) Int. Cl.

| | | |
|---|---|---|
| *B06B 1/06* | (2006.01) | |
| *G10K 11/02* | (2006.01) | |
| *B32B 7/12* | (2006.01) | |
| *H01L 41/083* | (2006.01) | |
| *G10K 9/122* | (2006.01) | |
| *G10K 11/30* | (2006.01) | |
| *A61B 8/00* | (2006.01) | |

(52) U.S. Cl.
CPC .............. *G10K 9/122* (2013.01); *G10K 11/02* (2013.01); *G10K 11/30* (2013.01); *H01L 41/083* (2013.01); *A61B 8/4209* (2013.01); *Y10T 156/10* (2015.01); *Y10T 428/31855* (2015.04)

(56) References Cited

U.S. PATENT DOCUMENTS

| | | |
|---|---|---|
| 4,484,820 A | 11/1984 | Rosencwaig |
| 4,523,122 A | 6/1985 | Tone et al. |
| 4,651,850 A | 3/1987 | Matsuo |
| 4,672,963 A | 6/1987 | Barken |
| 4,699,150 A | 10/1987 | Kawabuchi et al. |
| 4,856,335 A | 8/1989 | Tornberg |
| 5,050,128 A | 9/1991 | Saitoh et al. |
| 5,070,733 A | 12/1991 | Nagata et al. |
| 5,136,172 A | 8/1992 | Nakata et al. |
| 5,235,553 A | 8/1993 | Garlick et al. |
| 5,265,612 A | 11/1993 | Sarvazyan et al. |
| 5,353,798 A | 10/1994 | Sieben |
| 5,365,024 A | 11/1994 | Hasegawa et al. |
| 5,553,035 A | 9/1996 | Seyed-Bolorforosh et al. |
| 5,577,507 A | 11/1996 | Snyder et al. |
| 5,713,356 A | 2/1998 | Kruger |
| 5,718,231 A | 2/1998 | Dewhurst et al. |
| 5,800,350 A | 9/1998 | Coppleson et al. |
| 5,840,023 A | 11/1998 | Oraevsky et al. |
| 5,971,925 A | 10/1999 | Hossack et al. |
| 5,991,693 A | 11/1999 | Zalewski |
| 6,102,857 A | 8/2000 | Kruger et al. |
| 6,104,942 A | 8/2000 | Kruger |
| 6,182,341 B1 | 2/2001 | Talbot et al. |
| 6,183,578 B1 | 2/2001 | Ritter et al. |
| 6,194,814 B1 | 2/2001 | Hanafy et al. |
| 6,216,025 B1 | 4/2001 | Kruger |
| 6,246,898 B1 | 6/2001 | Vesely et al. |
| 6,292,682 B1 | 9/2001 | Kruger |
| 6,443,900 B2 | 9/2002 | Adachi et al. |
| 6,490,470 B1 | 12/2002 | Kruger |
| 6,498,942 B1 | 12/2002 | Esenaliev et al. |
| 6,519,376 B2 | 2/2003 | Biagi et al. |
| 6,551,247 B2 | 4/2003 | Saito et al. |
| 6,567,688 B1 | 5/2003 | Wang |
| 6,633,774 B2 | 10/2003 | Kruger |
| 6,645,144 B1 | 11/2003 | Wen et al. |
| 6,851,392 B2 | 2/2005 | Zan et al. |
| 6,979,282 B1 | 12/2005 | Mangano |
| 7,052,460 B2 | 5/2006 | Liu et al. |
| 7,133,713 B2 | 11/2006 | Zan |
| 7,139,676 B2 | 11/2006 | Barford |
| 7,230,368 B2 | 6/2007 | Lukacs et al. |
| 7,245,789 B2 | 7/2007 | Bates et al. |
| 7,266,407 B2 | 9/2007 | Li et al. |
| 7,367,948 B2 | 5/2008 | O'Donnell et al. |
| 7,426,904 B2 | 9/2008 | Zan et al. |
| 7,447,388 B2 | 11/2008 | Bates et al. |
| 7,713,200 B1 | 5/2010 | Sarvazyan et al. |
| 7,750,536 B2 | 7/2010 | Chaggares et al. |
| 7,774,042 B2 | 8/2010 | Kruger |
| 7,798,705 B2 | 9/2010 | Burgholzer et al. |
| 7,808,156 B2 | 10/2010 | Chaggares et al. |
| 8,078,256 B2 | 12/2011 | Zan |
| 8,343,289 B2 | 1/2013 | Chaggares et al. |
| 8,529,454 B2 | 9/2013 | Chen |
| 8,847,467 B2 | 9/2014 | Chaggares et al. |
| 9,520,119 B2 * | 12/2016 | Chaggares .............. B06B 1/067 |
| 9,791,417 B2 | 10/2017 | Irisawa et al. |
| 2001/0041842 A1 | 11/2001 | Eberle et al. |
| 2001/0055435 A1 | 12/2001 | Biagi et al. |
| 2002/0007118 A1 | 1/2002 | Adachi et al. |
| 2002/0035271 A1 | 3/2002 | Kruger |
| 2002/0111620 A1 | 8/2002 | Cooper et al. |
| 2002/0193678 A1 | 12/2002 | Kruger |
| 2003/0032884 A1 | 2/2003 | Smith et al. |
| 2003/0069491 A1 | 4/2003 | Kruger |
| 2003/0187356 A1 | 10/2003 | Wakabayashi et al. |
| 2003/0203304 A1 | 10/2003 | Katagiri et al. |
| 2004/0000847 A1 | 1/2004 | Ladabaum et al. |
| 2004/0040379 A1 | 3/2004 | O'Donnell et al. |
| 2004/0054287 A1 | 3/2004 | Stephens |
| 2004/0067000 A1 | 4/2004 | Bates et al. |
| 2004/0095045 A1 | 5/2004 | Baumgartner |
| 2004/0122319 A1 | 6/2004 | Mehi et al. |
| 2004/0127783 A1 | 7/2004 | Kruger |
| 2004/0215072 A1 | 10/2004 | Zhu |
| 2004/0236219 A1 | 11/2004 | Liu et al. |
| 2005/0004458 A1 | 1/2005 | Kanayama et al. |
| 2005/0070803 A1 | 3/2005 | Cullum et al. |
| 2005/0101854 A1 | 5/2005 | Larson et al. |
| 2005/0107692 A1 | 5/2005 | Li et al. |
| 2005/0127793 A1 | 6/2005 | Baumgartner et al. |
| 2005/0187471 A1 | 8/2005 | Kanayama et al. |
| 2005/0240102 A1 | 10/2005 | Rachlin et al. |
| 2005/0272183 A1 | 12/2005 | Lukacs et al. |
| 2006/0055486 A1 | 3/2006 | Nakatsuka et al. |
| 2006/0184042 A1 | 8/2006 | Wang et al. |
| 2007/0016071 A1 | 1/2007 | Eberle et al. |
| 2007/0049829 A1 | 3/2007 | Kaminski et al. |
| 2007/0093702 A1 | 4/2007 | Yu et al. |
| 2007/0121697 A1 | 5/2007 | Burgholzer et al. |
| 2007/0133925 A1 | 6/2007 | Bates et al. |
| 2007/0182287 A1 | 8/2007 | Lukacs et al. |
| 2007/0205697 A1 | 9/2007 | Chaggares et al. |
| 2007/0205698 A1 | 9/2007 | Chaggares et al. |
| 2007/0239001 A1 | 10/2007 | Mehi et al. |
| 2007/0249916 A1 | 10/2007 | Pesach et al. |
| 2008/0108867 A1 | 5/2008 | Zhou |
| 2008/0123083 A1 | 5/2008 | Wang et al. |
| 2008/0156577 A1 | 7/2008 | Dietz et al. |
| 2008/0173093 A1 | 7/2008 | Wang et al. |
| 2008/0194965 A1 | 8/2008 | Sliwa et al. |
| 2008/0221647 A1 | 9/2008 | Chamberland et al. |
| 2009/0024038 A1 | 1/2009 | Arnold |
| 2009/0024040 A1 | 1/2009 | Cespedes |
| 2009/0048489 A1 | 2/2009 | Igarashi et al. |
| 2009/0054763 A1 | 2/2009 | Wang et al. |
| 2009/0105588 A1 | 4/2009 | Emelianov et al. |
| 2009/0112098 A1 | 4/2009 | Vaezy et al. |
| 2009/0124902 A1 | 5/2009 | Herrmann |
| 2009/0187099 A1 | 7/2009 | Burcher |
| 2009/0227997 A1 | 9/2009 | Wang et al. |
| 2009/0240149 A1 | 9/2009 | Peyman |
| 2009/0281431 A1 | 11/2009 | Phillips et al. |
| 2009/0324890 A1 | 12/2009 | Wu et al. |
| 2010/0016717 A1 | 1/2010 | Dogra et al. |
| 2010/0028261 A1 | 2/2010 | Emelianov et al. |
| 2010/0037695 A1 | 2/2010 | Tsujita et al. |
| 2010/0041987 A1 | 2/2010 | Manohar et al. |
| 2010/0049044 A1 | 2/2010 | Burcher |
| 2010/0053618 A1 | 3/2010 | Nakajima et al. |
| 2010/0087732 A1 | 4/2010 | Eberle et al. |
| 2010/0094134 A1 | 4/2010 | Zhu et al. |
| 2010/0156244 A1 | 6/2010 | Lukacs et al. |
| 2010/0196278 A1 | 8/2010 | Tomida |

(56) References Cited

U.S. PATENT DOCUMENTS

| | | |
|---|---|---|
| 2010/0208965 A1 | 8/2010 | Jiang et al. |
| 2010/0245766 A1 | 9/2010 | Zhang et al. |
| 2010/0245769 A1 | 9/2010 | Zhang et al. |
| 2010/0245770 A1 | 9/2010 | Zhang et al. |
| 2010/0249562 A1 | 9/2010 | Zhang et al. |
| 2010/0249570 A1 | 9/2010 | Carson et al. |
| 2010/0268042 A1 | 10/2010 | Wang et al. |
| 2010/0268058 A1 | 10/2010 | Chen |
| 2010/0298688 A1 | 11/2010 | Dogra et al. |
| 2010/0298689 A1 | 11/2010 | Wang |
| 2010/0331662 A1 | 12/2010 | Fukutani et al. |
| 2011/0021924 A1 | 1/2011 | Sethuraman et al. |
| 2011/0044516 A1 | 2/2011 | Li et al. |
| 2011/0045607 A1 | 2/2011 | Li et al. |
| 2011/0054292 A1 | 3/2011 | Hirson et al. |
| 2011/0054294 A1 | 3/2011 | Kruger |
| 2011/0066023 A1 | 3/2011 | Kanayama et al. |
| 2011/0081294 A1 | 4/2011 | Fukui et al. |
| 2011/0088477 A1 | 4/2011 | Someda et al. |
| 2011/0117023 A1 | 5/2011 | Yamauchi et al. |
| 2011/0128816 A1 | 6/2011 | Baba et al. |
| 2011/0144496 A1 | 6/2011 | Li et al. |
| 2011/0144502 A1 | 6/2011 | Zhou et al. |
| 2011/0262750 A1 | 10/2011 | Taima |
| 2012/0029353 A1 | 2/2012 | Slayton et al. |
| 2013/0190591 A1 | 7/2013 | Hirson et al. |
| 2013/0289381 A1 | 10/2013 | Oraevsky et al. |
| 2014/0345385 A1 | 11/2014 | Irisawa et al. |
| 2015/0108874 A1 | 4/2015 | Chaggares et al. |
| 2015/0173625 A1 | 6/2015 | Chaggares et al. |
| 2015/0257734 A1 | 9/2015 | Chaggares |

FOREIGN PATENT DOCUMENTS

| | | |
|---|---|---|
| CN | 101268953 A | 9/2008 |
| CN | 101442940 A | 5/2009 |
| CN | 103209643 A | 7/2013 |
| EP | 0413330 A2 | 2/1991 |
| EP | 0413330 A3 | 2/1991 |
| EP | 0413330 B1 | 2/1991 |
| EP | 1602331 A1 | 12/2005 |
| EP | 1935346 A1 | 6/2008 |
| EP | 2110076 A1 | 10/2009 |
| EP | 2180352 A1 | 4/2010 |
| JP | 54013370 U | 1/1979 |
| JP | 56086598 | 7/1981 |
| JP | 58171665 | 10/1983 |
| JP | 61172546 U | 8/1986 |
| JP | 61278297 A | 12/1986 |
| JP | 62097245 A | 5/1987 |
| JP | 0283481 | 3/1990 |
| JP | 02260999 | 10/1990 |
| JP | 04040099 U | 2/1992 |
| JP | 07159379 A | 6/1995 |
| JP | 07159381 A | 6/1995 |
| JP | 09107594 | 4/1997 |
| JP | 11206759 A | 8/1999 |
| JP | 2000292416 A | 10/2000 |
| JP | 2001069594 | 3/2001 |
| JP | 2003295496 A | 10/2003 |
| JP | 3495069 B2 | 2/2004 |
| JP | 2004020986 | 3/2004 |
| JP | 2004351023 A | 12/2004 |
| JP | 2005198261 | 7/2005 |
| JP | 2005218684 A | 8/2005 |
| JP | 3745157 B2 | 2/2006 |
| JP | 2006208050 A | 8/2006 |
| JP | 2006242816 A | 9/2006 |
| JP | 3894024 B2 | 3/2007 |
| JP | 2007097654 A | 4/2007 |
| JP | 2009031268 A | 2/2009 |
| JP | 3256362 U | 12/2009 |
| JP | 2010022816 A | 2/2010 |
| JP | 2010057730 A | 3/2010 |
| JP | 2010075681 A | 4/2010 |
| JP | 2010088627 | 4/2010 |
| JP | 2010104816 | 5/2010 |
| JP | 2010136887 A | 6/2010 |
| JP | 2011005042 | 1/2011 |
| KR | 101222198 B1 | 1/2013 |
| KR | 20130123347 A | 11/2013 |
| TW | I240990 B | 10/2005 |
| TW | I328972 B | 8/2010 |
| TW | M458203 U | 8/2013 |
| WO | 1994014379 A1 | 7/1994 |
| WO | 1998014118 A1 | 4/1998 |
| WO | 2000022987 A2 | 4/2000 |
| WO | 2000045707 A2 | 8/2000 |
| WO | 2001010298 | 2/2001 |
| WO | 2004032746 A2 | 4/2004 |
| WO | 2004042382 | 5/2004 |
| WO | 2005048840 A1 | 6/2005 |
| WO | 2005104210 | 11/2005 |
| WO | 2006007611 A1 | 1/2006 |
| WO | 2006061829 A1 | 6/2006 |
| WO | 2007072490 A1 | 6/2007 |
| WO | 2007084981 A2 | 7/2007 |
| WO | 2007100937 A2 | 9/2007 |
| WO | 2007103143 | 9/2007 |
| WO | 2007103144 | 9/2007 |
| WO | 2007117572 A2 | 10/2007 |
| WO | 2007084981 A3 | 11/2007 |
| WO | 2007148239 A2 | 12/2007 |
| WO | 2008011112 | 1/2008 |
| WO | 2007148239 A3 | 2/2008 |
| WO | 2008066962 A1 | 6/2008 |
| WO | 2008067438 A1 | 6/2008 |
| WO | 2008075299 A1 | 6/2008 |
| WO | 2008075961 A2 | 6/2008 |
| WO | 2007100937 A3 | 7/2008 |
| WO | 2008067438 A3 | 7/2008 |
| WO | 2007117572 A3 | 8/2008 |
| WO | 2008097527 | 8/2008 |
| WO | 2008100386 A2 | 8/2008 |
| WO | 2008101019 A2 | 8/2008 |
| WO | 2008103982 A2 | 8/2008 |
| WO | 2008100386 A3 | 10/2008 |
| WO | 2008103982 A3 | 10/2008 |
| WO | 2008101019 A3 | 11/2008 |
| WO | 2008143200 | 11/2008 |
| WO | 2008075961 A3 | 12/2008 |
| WO | 2009011884 A1 | 1/2009 |
| WO | 2009011934 A1 | 1/2009 |
| WO | 2009045885 A2 | 4/2009 |
| WO | 2009055705 A2 | 4/2009 |
| WO | 2009063424 A1 | 5/2009 |
| WO | 2009064030 A1 | 5/2009 |
| WO | 2009045885 A3 | 6/2009 |
| WO | 2009055705 A3 | 6/2009 |
| WO | 2009073979 A1 | 6/2009 |
| WO | 2009076427 | 6/2009 |
| WO | 2009103502 A1 | 8/2009 |
| WO | 2009154298 A1 | 12/2009 |
| WO | 2009158146 | 12/2009 |
| WO | 20090154963 A1 | 12/2009 |
| WO | 2010009412 A2 | 1/2010 |
| WO | 2009158146 A3 | 3/2010 |
| WO | 2010027095 A1 | 3/2010 |
| WO | 2010030817 A1 | 3/2010 |
| WO | 2010039950 A1 | 4/2010 |
| WO | 2010045421 A2 | 4/2010 |
| WO | 2010048623 A2 | 4/2010 |
| WO | 2010048623 A8 | 4/2010 |
| WO | 2010067608 A1 | 6/2010 |
| WO | 2010045421 A3 | 7/2010 |
| WO | 2010086861 A1 | 8/2010 |
| WO | 2010107930 A1 | 9/2010 |
| WO | 2010107933 A1 | 9/2010 |
| WO | 2010048623 A9 | 10/2010 |
| WO | 2010048623 A3 | 11/2010 |
| WO | 2010127199 A2 | 11/2010 |
| WO | 2010135469 A1 | 11/2010 |
| WO | 2011000389 A1 | 1/2011 |
| WO | 2011012274 A1 | 2/2011 |

(56) References Cited

FOREIGN PATENT DOCUMENTS

| WO | 2010009412 A3 | 3/2011 |
|---|---|---|
| WO | 2011035279 A2 | 3/2011 |
| WO | 2011053931 A2 | 5/2011 |
| WO | 2011074102 A1 | 6/2011 |
| WO | 2011137385 | 11/2011 |
| WO | 2013121743 A1 | 8/2013 |
| WO | 2013145764 | 10/2013 |
| WO | 2015095721 | 6/2015 |
| WO | 2015138796 | 9/2015 |

OTHER PUBLICATIONS

DuPont Titanium Technologies, "Polymers, Light & Science," DuPont Ti-Pure Titanium Dioxide. www.chemours.com/Titanium-5FTechnologies/es-5FUS/tech-5Finfo/literature/Plastics/PL-5FB-5FPolymers-5FLight-5FScience, pp. 1-20, Jun. 2007, US.
State Intellectual Property Office, Second Office Action, Chinese Patent Application CN 201180031854.0, dated May 18, 2015, 4 pages.
European Patent Office, Extended European Search Report, EP Patent Application 15762059.2, dated Nov. 30, 2017, 9 pages.
European Patent Office, Partial European Search Report, EP Patent Application 14870691.4, dated Jan. 19, 2018, 12 pages.
C-Lec Plastice Inc., "Rexolite, High Voltage, High Performance Plastic: Rexolite Specifications," copyright 2005, 3 pages.
U.S. Appl. No. 61/174,571, filed May 1, 2009, Hirson et al.
Callens, D. et al. "Matching ultrasonic transducer using two matching layers where one of them is glue," NDT & E International, Butterworth-Heinemann, Oxford, GB, Dec. 1, 2004, vol. 37, No. 8, pp. 591-596.
Canadian Intellectual Property Office, Examiner's Report, CA Patent Application 2,644,224, dated Jan. 7, 2014, 2 pages.
Canadian Intellectual Property Office, Examiner's Report, CA Patent Application 2,644,224, dated Oct. 6, 2014, 4 pages.
Extended Search Report, European Patent Application No. EP07752028.6, dated Mar. 29, 2012, 7 pages.
Farquhar and Steinwall. "Elastic Properties of Filled Epoxy Encapsulants," EEP vol. 10-2, Advances in Electronic Packaging. ASME, 1995.
First Office Action for Chinese Patent Application No. CN200780016016.X, dated Jun. 8, 2010, 8 pages.
Grewe, Gururafa, Newnharn, and Shrout "Acoustic Properties of Particle/Polymer Composites for Transducer Backing Applications," IEEE Trans. on Ultrasonics, Ferroelectrics and Frequency Control, 37(6): 506-514, 1990.
International Search Report and Written Opinion, PCT Patent Application PCT/US2007/05300, dated Feb. 14, 2008, 7 pages.
International Search Report and Written Opinion, PCT Patent Application PCT/US2007/05301 dated Feb. 20, 2008, 7 pages.
Japan Patent Office, Final Rejection, JP Patent Application 2008-557385, dated Jan. 9, 2013, 5 pages.
Japan Patent Office, Final Rejection, JP Patent Application 2013-099049, dated Oct. 29, 2014, 6 pages.
Japan Patent Office, Notice of Reasons for Rejection, JP Patent Application 2008-557385, dated Aug. 6, 2012, 7 pages.
Japan Patent Office, Notice of Reasons for Rejection, JP Patent Application 2012-087397, dated Aug. 6, 2014, 11 pages.
Japan Patent Office, Notice of Reasons for Rejection, JP Patent Application 2012-087397, dated Dec. 17, 2013, 7 pages.
Japan Patent Office, Notice of Reasons for Rejection, JP Patent Application 2013-099049, dated Dec. 17, 2013, 6 pages.
Notice of Reasons for Rejection for Japanese Patent Application JP 2008-557385, dated Oct. 6, 2011, 6 pages.
Ritter, Shung, Gang, Lopath, Tutwiler, and Shrout. "Proceedings of SPIE" vol. 3664 Medical Imaging 1999: Ultrasonic Transducer Engineering, K.Kirk Shung, editor, pp. 67-75, Jun. 1999.
Second Office Action for Chinese Patent Application No. CN200780016016.X, dated Jan. 12, 2011, 16 pages.
Selfridge. "Approximate Material Properties in Isotropic Materials," IEE Trans Sonics and Ultrasonics, vol. SU-32, No. 3, May 1985.
Wang, Ritter, Cao, and Shung. "Passive Materials for High Frequency Ultrasound Transducers," SPIE Conf. on Ultrasonic Transducer Engineering, San Diego, California, SPIE vol. 3664, Feb. 1999.
Japan Patent Office, Official Action, JP Patent Application 2013-508293, dated Jan. 26, 2015, 7 pages.
European Patent Office, Supplementary European Search Report, EP Patent Application 11775660.1, dated Dec. 16, 2013, 8 pages.
International Searching Authority, International Search Report, PCT Application PCT/US2011/034640, dated Aug. 8, 2011, 2 pages.
International Searching Authority, Written Opinion, PCT Application PCT/US2011/034640, dated Aug. 8, 2011, 8 pages.
Oraevsky, A.A. et al. "Laser-based optoacoustic imaging in biological tissues." Proc. SPIE vol. 2134A, p. 122-128, Laser-Tissue Interaction V, Steven L. Jacques, Ed., Aug. 1994.
State Intellectual Property Office, First Office Action, Chinese Patent Application CN 201180031854.0, dated Sep. 28, 2014, 13 pages.
Third Office Action for Chinese Patent Application No. CN200780016016.X, dated Jul. 6, 2011, 3 pages.
Fourth Office Action for Chinese Patent Application No. CN200780016016.X, dated Oct. 26, 2011, 3 pages.
International Searching Authority, International Search Report and Written Opinion, International Application PCT/US2014/071533, dated Apr. 20, 2015, 19 pages.
International Searching Authority, International Search Report and Written Opinion, International Application PCT/US2015/020279, dated Jun. 19, 2015, 14 pages.
Taiwan Intellectual Property Office, Examination Opinion, TW Patent Application 103144411, dated Nov. 15, 2016, 24 pages (with English translation).
Japanese Patent Office, Notice of Final Rejection, JP Patent Application 2015-219452, dated Apr. 2, 2018, 16 pages; with English translation.
Japanese Patent Office, Office Action, JP Patent Application 2015-219452, dated May 19, 2017, 13 pages; with English translation.

* cited by examiner

HIGH FREQUENCY ULTRASONIC TRANSDUCER AND MATCHING LAYER COMPRISING CYANOACRYLATE

BACKGROUND

Small animal imaging is an important field of research in many areas including preclinical pharmaceutical development, developmental biology, cardiac research, and molecular biology. Several small animal models are widely used in these fields, the most prevalent being the mouse and the rat. High frequency ultrasound has been widely used to image the mouse model at frequencies from about 20 megahertz (MHz) to over 60 MHz. The rat model, however, is difficult to image at high frequencies in comparison to the mouse because the rat has highly attenuating and echogenic epidermal, dermal, and subdermal tissues.

SUMMARY

In one aspect, matching layers for an ultrasonic transducer stack having a plurality of layers are provided. A matching layer can comprise a composite material comprising a matrix material loaded with a plurality of micron-sized and nano-sized particles. In another aspect, the composite material can also comprise a matrix material loaded with a plurality of heavy and light particles. In a further aspect, a matching layer can also comprise cyanoacrylate.

Also provided are ultrasound transducer stacks comprising a plurality of layers, each layer having a top surface and an opposed bottom surface, wherein the plurality of layers includes a piezoelectric layer and at least one matching layer. The matching layers can be positioned in the stack to overlie the top surface of the piezoelectric layer. An exemplary stack can comprise a matching layer comprising a composite material loaded with a plurality of nano and micron sized particles, a matching layer with a plurality of heavy and light particles and a matching layer comprising cyanoacrylate.

Other systems, methods, and aspects and advantages of the invention will be discussed with reference to the FIGS. and to the detailed description.

BRIEF DESCRIPTION OF THE DRAWINGS

The accompanying drawings, which are incorporated in and constitute a part of this specification, illustrate certain aspects of the instant invention and together with the description, serve to explain, without limitation, the principles of the invention. Like reference characters used therein indicate like parts throughout the several drawings.

DETAILED DESCRIPTION

Figure 1:
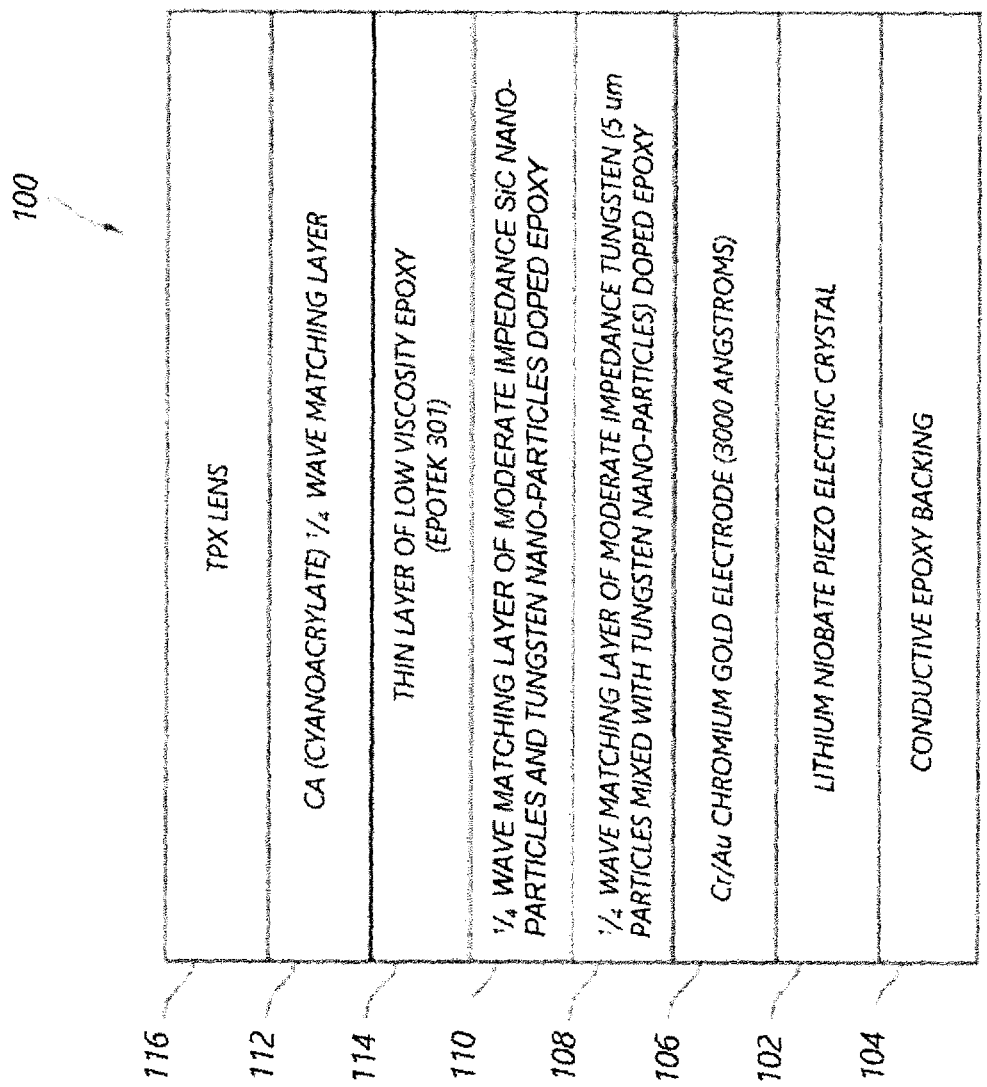
FIG. 1 is a schematic diagram illustrating an exemplary transducer stack having a plurality of layers, and showing a plurality of matching layers.
Figure 2:
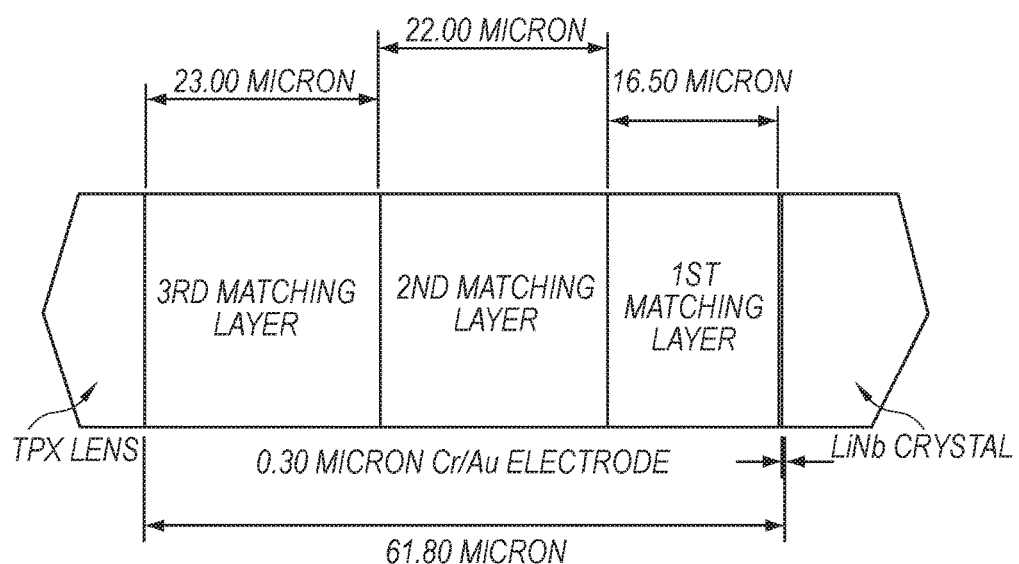
FIG. 2 is a schematic diagram showing a cross section of an exemplary transducer stack in the elevational dimension.
Figure 3:
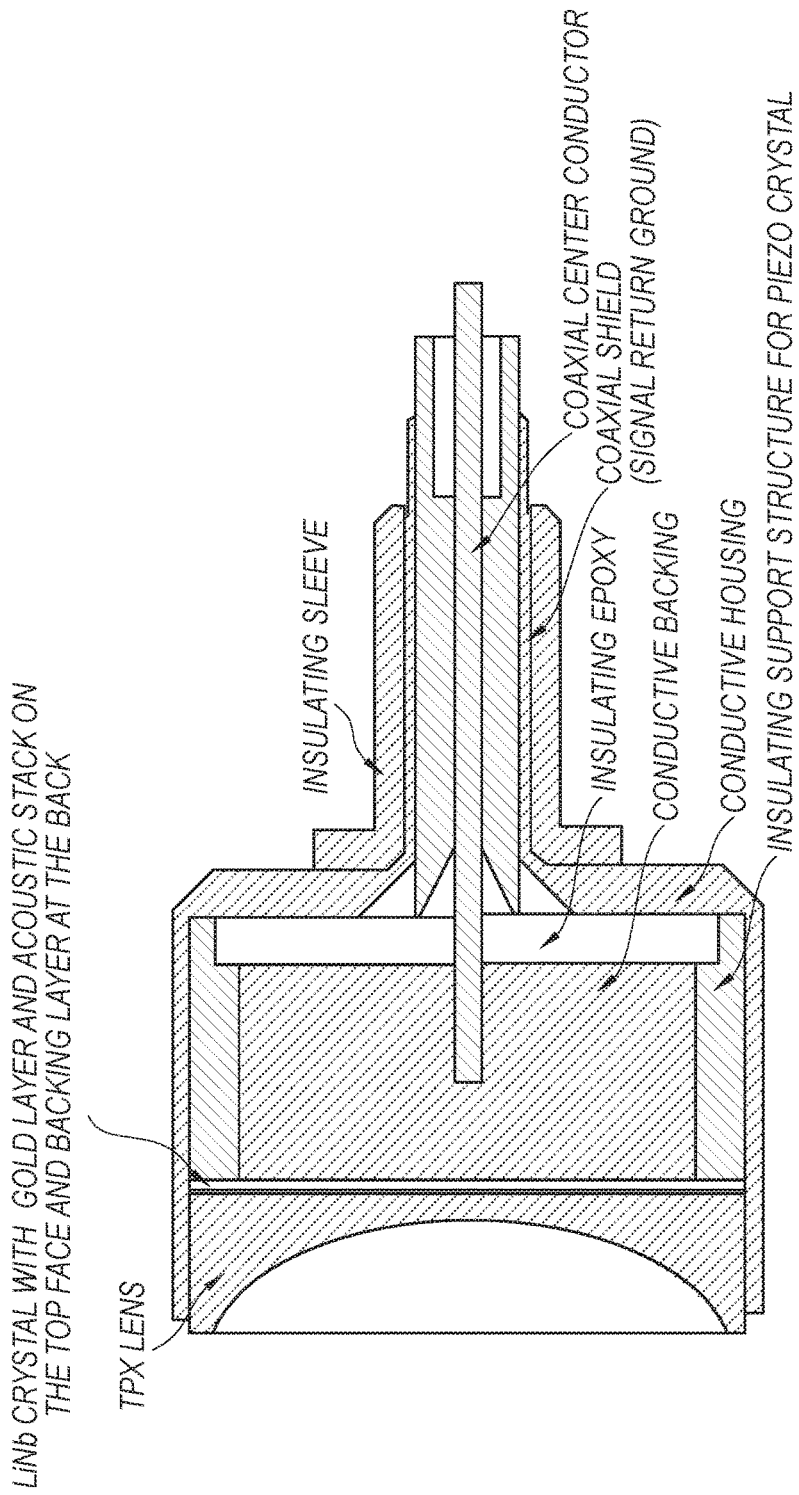
FIG. 3 is a block schematic diagram illustrating an exemplary transducer stack with electrical connections.
Figure 4:
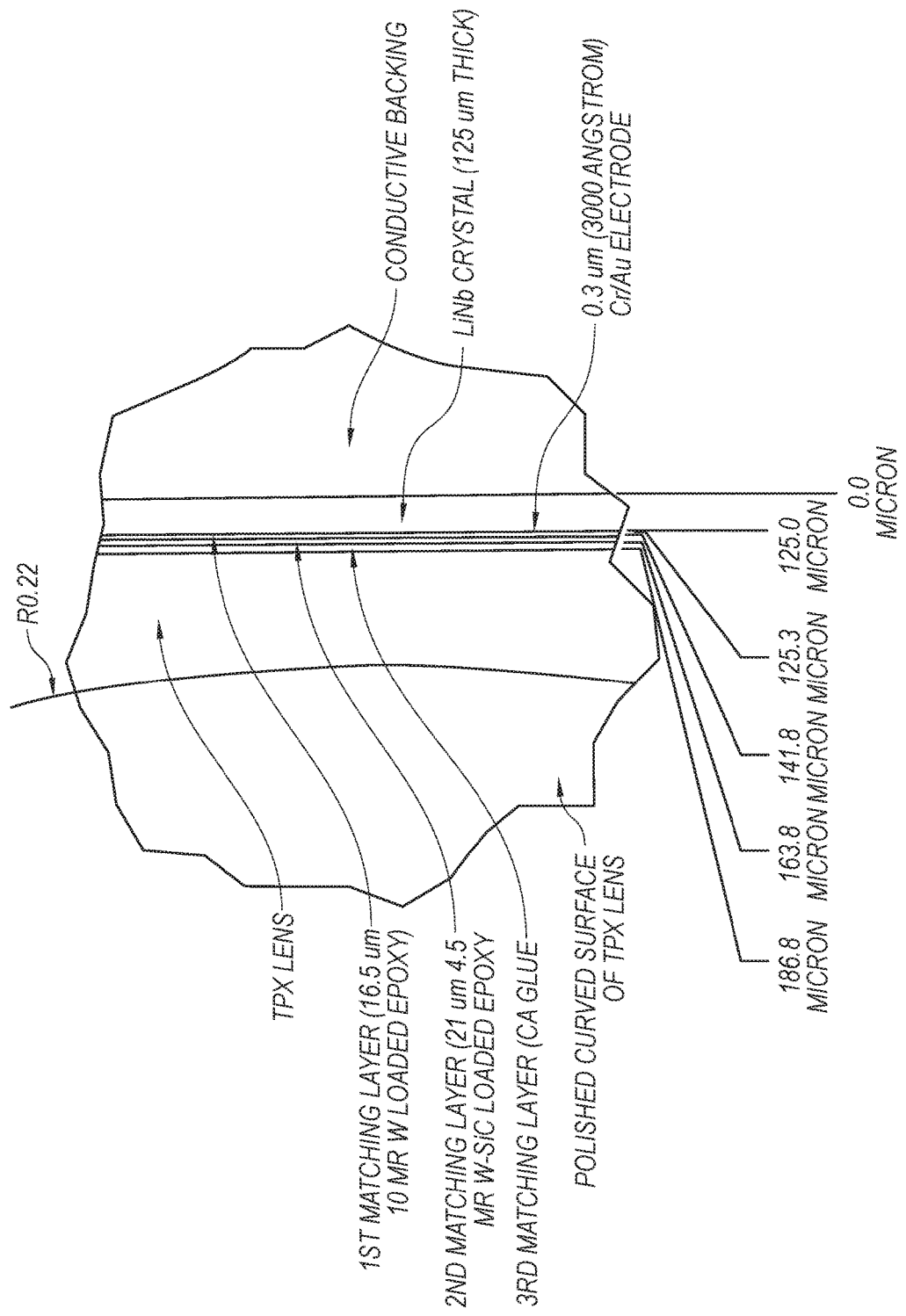
FIG. 4 is an enlarged schematic diagram illustrating layers of the exemplary transducer stack of FIG. 3, shown in exemplary scaled dimensions.

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof As used herein, the singular forms "a," "an" and "the" include plural referents unless the context clearly dictates otherwise. Thus, for example, reference to a "layer" includes aspects having two or more such layers unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

By a "subject" is meant an individual. The term subject includes small or laboratory animals as well as primates, including humans. A laboratory animal includes, but is not limited to, a rodent such as a mouse or a rat. The term laboratory animal is also used interchangeably with animal, small animal, small laboratory animal, or subject, which includes mice, rats, cats, dogs, fish, rabbits, guinea pigs, rodents, etc. The term laboratory animal does not denote a particular age or sex. Thus, adult and newborn animals, as well as fetuses (including embryos), whether male or female, are included.

The present invention may be understood more readily by reference to the following detailed description of preferred embodiments of the invention and the examples included therein and to the Figures and their previous and following description.

In one embodiment, the present invention is directed to matching layers for ultrasonic transducer stacks having a plurality of layers. Ultrasound transducers, or transducer stacks, that are used for imaging utilize acoustic matching layers positioned between a piezoelectric layer and a lens layer or face layer of the transducer. The piezoelectric layer typically has a high acoustic impedance (Z). The subject being imaged typically has a much lower acoustic impedance. If the piezoelectric layer were pressed directly onto the subject, a great deal of the acoustic energy would be lost due to the impedance mismatch between the piezoelectric layer and the subject. In the ultrasound imaging arts, matching layers with acoustic impedances between the piezoelectric layer and the lens or face layer are introduced into the transducer stack to provide a transition from the higher impedance piezoelectric layer to the lower impedance subject.

Thus, the matching layers provided herein can be used in an ultrasonic transducer stack to accomplish an impedance transition from a piezoelectric layer to a lens or face layer. The exemplary matching layers can have varying acoustic impedances. One exemplary matching layer can have an acoustic impedance of between about 7.0 MegaRayles and about 14.0 MegaRayles. Another exemplary matching layer can have an acoustic impedance of between about 3.0 MegaRayles and about 7.0 MegaRayles. Yet another exemplary matching layer can have an acoustic impedance of between about 2.5 MegaRayles and about 2.8 MegaRayles. One skilled in the art will appreciate that each exemplary matching layer can be a ¼ wavelength matching layer.

An ultrasonic transducer stack can be used to generate, transmit and receive ultrasound of high frequency (equal to or greater than 20 megahertz). Exemplary ultrasonic transducer stacks comprise at least one disclosed matching layer.

A schematic of such an exemplary transducer stack is shown in FIG. 1. FIG. 1 shows a transducer stack 100 having a lithium nibate piezoelectric layer 102. The bottom surface of the piezoelectric layer overlies the top surface of a backing layer 104. Above the top layer of the piezoelectric layer are an electrode layer 106, three exemplary matching layers (108, 110 and 112), an epoxy bonding layer 114, and a lens layer 116.

In this aspect, the matching layer 108 is a higher impedance matching layer that can have an acoustic impedance of between about 7.0 MegaRayles and about 14.0 MegaRayles. In another aspect, the matching layer 108 can comprise nano and micron sized particles as described below.

Above the upper surface of the matching layer 108 is the matching layer 110, which has a lower impedance than the matching layer 108. The matching layer 110 can have an acoustic impedance of between about 3.0 MegaRayles and about 7.0 MegaRayles. In another aspect, the matching layer 110 can comprise light and heavy particles as described below.

The matching layer 112 has a lower impedance than the matching layer 110. The matching layer 112 has an acoustic impedance of between about 2.5 MegaRayles and about 2.8 MegaRayles. The matching layer 112 can comprise cyanoacrylate as described below. The matching layer 112 can be bonded to the underlying matching layer 110 using a layer of epoxy 114.

The face layer of the exemplary transducer stack 100 comprises a lens layer 116. The lens layer can comprise TPX as described below. The lens layer 116 can be directly bonded to the matching layer 112. Thus, in this exemplary transducer stack 100 the matching layers (108, 110, and 112) accomplish an impedance transition from a piezoelectric layer 102 to a lens layer 116.

A transducer stack, as exemplified herein, can be used to image subjects, or anatomical portions thereof, using high frequency ultrasound. The images produced can have a high resolution. In one aspect, an ultrasonic transducer stack comprises a plurality of layers, each layer having a top surface and an opposed bottom surface. In another aspect, the plurality of layers includes a piezoelectric layer and at least one matching layer. When positioned in a transducer stack, the bottom surface of a given matching layer overlies the top surface of the piezoelectric layer.

A matching layer can comprise a composite material. In one aspect, the composite material can comprise a matrix material loaded with a plurality of micron-sized and nano-sized particles. In another aspect, the composite material can also comprise a matrix material loaded with a plurality of first heavy particles and a plurality of second light particles. In a further aspect, a matching layer can also comprise cyanoacrylate (CA).

Capturing of ultrasound data using an exemplary transducer stack comprises generating ultrasound, transmitting ultrasound into the subject, and receiving ultrasound reflected by the subject. A wide range of frequencies of ultrasound can be used to capture ultrasound data. For example, clinical frequency ultrasound (less than 20 MHz) or high frequency ultrasound (equal to or greater than 20 MHz) can be used. One skilled in the art can readily determine what frequency to use based on factors such as, for example, but not limited to, depth of imaging, or desired resolution.

High frequency ultrasound may be desired when high resolution imaging is desired and the structures to be imaged within the subject are not at too great a depth. Thus, capturing ultrasound data can comprise transmitting ultrasound having a frequency of at least 20 MHz into the subject and receiving a portion of the transmitted ultrasound that is reflected by the subject. For example, a transducer having a center frequency of about 20 MHz, 30 MHz, 40 MHz, 50 MHz, 60 MHz or higher can be used. In one exemplary preferred embodiment, the transducer can have a center frequency of about 20 MHz (for a design frequency of 25 MHz per the general frequency example given herein below).

High frequency ultrasound transmission is often desirable for the imaging of small animals, where a high resolution may be achieved with an acceptable depth of penetration. The methods can therefore be used at clinical or high frequency on a small animal subject. Optionally, as noted above, the small animal can be a rat or mouse.

The disclosed transducers can be operatively connected to an ultrasound imaging system for the generation, transmission, receipt, and processing of ultrasound data. For example, ultrasound can be transmitted, received and processed using an ultrasonic scanning device that can supply an ultrasonic signal of at least about 20 MHz to the highest practical frequency. Any ultrasound system or device capable of operating at 20 MHz or above can be used.

The matching layers described herein can be used with other devices capable of transmitting and receiving ultrasound at the desired frequencies. For example, ultrasound systems using arrayed transducers can be used.

If a small animal subject is imaged, it can exemplarily be positioned on a platform with access to anesthetic equipment. Thus, the methods can be used with platforms and apparatus used in imaging small animals including "rail guide" type platforms with maneuverable probe holder apparatuses. For example, the described systems can be used with multi-rail imaging systems, and with small animal mount assemblies as described in U.S. patent application Ser. No. 10/683,168, entitled "Integrated Multi-Rail Imaging System," U.S. patent application Ser. No. 10/053,748, entitled "Integrated Multi-Rail Imaging System," U.S. patent application Ser. No. 10/683,870, now U.S. Pat. No.

6,851,392, issued Feb. 8, 2005, entitled "Small Animal Mount Assembly," and U.S. patent application Ser. No. 11/053,653, entitled "Small Animal Mount Assembly," which are incorporated herein by reference.

Small animals can be anesthetized during imaging and vital physiological parameters such as heart rate and temperature can be monitored. Thus, the system can include means for acquiring ECG and temperature signals for processing and display. The system can also display physiological waveforms such as an ECG, respiration or blood pressure waveform.

Also provided is the use of the described transducers or matching layers in a system for producing an ultrasound image using line-based image reconstruction when a high frame rate is desired. One example of such a system may have the following components as described in U.S. patent application Ser. No. 10/736,232, U.S. patent application publication 20040236219, which is incorporated herein by reference. The disclosed system for producing an ultrasound image using line based image reconstruction can provide an ultrasound image having an effective frame rate in excess of 200 frames per second. The system comprises an ECG based technique that enables high time resolution and allows the accurate depiction of a rapidly moving structure, such as a heart, in a small animal, such as a mouse, rat, rabbit, or other small animal, using ultrasound.

Many different organs of interest can be imaged including dynamic organs having a lumen. For example, a heart, or a portion thereof, can be imaged using the methods and systems described herein. The methods and systems are not limited to imaging the heart, however, and it is contemplated that other organs or portions thereof, including other portions of the cardiovascular system can be imaged.

Several small animal models are widely used in research, the most prevalent being the mouse and the rat. High frequency ultrasound has been used to image the mouse model with great effect at frequencies from about 20 MHz to over 60 MHz. However, the rat model has proved difficult to image at high frequencies in comparison to the mouse model due to highly attenuating and echogenic epidermal, dermal, and subdermal tissues, which give rise to two main imaging obstacles. The first is high attenuation of the high frequency ultrasonic energy. The second is the generation of multiple reflections that cause reverb imaging artifacts. Both of these obstacles can be mitigated by changing the operational characteristics of the transducer used to image the rat.

Exemplary operational characteristics that overcome these imaging obstacles can comprise high sensitivity to overcome attenuation, a matched lens system to overcome reverb, and/or the use of a matched attenuation layer between the transducer and the tissue to attenuate multiple reflections. In addition, the transducer described for imaging the rat can have a broad bandwidth, so as not to compromise axial resolution.

These three characteristics often come at the expense of each other and are generally regarded as engineering trade offs. In one example, more sensitivity generally comes at the expense of bandwidth. Similarly, better matching often involves lossy lens materials thus compromising sensitivity and, if designed to be a ¼ wave match at the design frequency, a reduction in bandwidth. The addition of a matched attenuation layer also results in reduced sensitivity of the primary signal level.

A transducer incorporating an acoustic match to water, sensitivity, and broad bandwidth response is described herein and is useful for the imaging of a subject animal model. The transducer improves high frequency ultrasonic imaging on rats and other small animal models.

In one aspect, to overcome the highly attenuative nature of the rat tissues, a highly efficient transducer with very good sensitivity is described herein. In a further aspect, the transducer is relatively broadband with, for example, a −6 dB bandwidth of about 80% or greater.

In another embodiment, matching layers for an ultrasonic transducer stack having a plurality of layers are provided. In one aspect, the matching layer described can be a layer of an ultrasonic transducer stack including a piezoelectric layer. In alternative aspects, the stack can comprise other layers, such as, for example and not meant to be limiting, a backing layer, other matching layers, a lens layer, a signal electrode layer, a ground electrode layer, bonding layers and/or other layers known to those skilled in the art.

In one embodiment of the present invention, a matching layer comprises a composite material. In this aspect, the composite material can comprise a matrix material loaded with a plurality of micron-sized and nano-sized particles. In an alternative aspect, the composite material can also comprise a matrix material loaded with a plurality of heavy and light particles. In another example, a matching layer can also comprise cured cyanoacrylate.

Exemplified herein are ultrasound transducer stacks that comprise a plurality of layers, each layer having a top surface and an opposed bottom surface. In one aspect, the plurality of layers includes a piezoelectric layer and at least one matching layer. In this aspect, the matching layers can be positioned in the stack such that they substantially overlie the top surface of the piezoelectric layer. An exemplary stack can comprise a matching layer comprising a composite material loaded with a plurality of nano and micron sized particles, a matching layer with a plurality of heavy and light particles and a matching layer comprising cyanoacrylate.

Piezoelectric materials that can be used include, for example and not meant to be limiting, ceramics, composite ceramic materials, and single crystals. For example, lithium niobate (LiNb) can be used for an exemplary single element mechanically scanned transducer. In another example, 36 degree Y-Rotated Lithium Niobate is an exemplary material for the piezoelectric layer. LiNb has a highly efficient mechanical coupling characteristic (Kt of about 50%), and a very low dielectric constant ($\in_r$=34) and can yield an efficient single element transducer that may not use an additional electrical matching network. Further, Lithium Niobate (LiNb) has a high Q (in the region of 10,000) that can result in a narrow band transducer. It is contemplated that the high Q can be compensated for with a broad band matching structure and a damping backing system, which acts to reduce the Q of the transducer.

In a further aspect, a backing system can be used with the transducer stack and can be connected to and/or underlie the bottom side piezoelectric layer. If used, a backing layer accomplishes several things. First, it has an acoustic impedance that causes the transducer to resonate with the desired bandwidth. Secondly, it is highly attenuating so that there are reduced or no internal reflections in the transducer itself. Finally, the backing layer can be in operative contact with the piezoelectric element.

In one exemplary aspect, the acoustic impedance of the backing layer is chosen as low as possible, relative to the Z of LiNb, to achieve high sensitivity while ensuring good bandwidth. For example, an acoustic impedance in the range of between about 5 MR to 7 MR gives a desirable trade-off between sensitivity and bandwidth. For example, should a higher bandwidth be desired, a backing impedance of between about 25 MR to 40 MR can be employed.

In regard to the attenuation of the backing layer, the higher the attenuation, the less backing thickness is required to eliminate internal reflections. Also, a thinner backing layer results in the transducer having less mass and volume.

In alternative aspects, the backing layer can be electrically conductive, or it can be an insulator. However, whether a conductor or insulator is used, the backing layer is operatively connected to the piezoelectric layer. The conductive backing layer can result in a faster manufacturing process, with a very narrow range of possible attenuation and acoustic impedances available. The non-conductive backing layer allows for a very wide range of damping and attenuation possibilities.

One exemplary backing layer is formed from Ablebond 16-1 conductive epoxy. This backing layer material has an acoustic impedance of about 6.7 MR and an attenuation of over about 100 dB/mm at 30 MHz. In addition, this exemplary conductive epoxy exhibits excellent conductivity at the bond line and makes an integral connection with the piezoelectric layer.

In alternative aspects, to create very high bandwidth designs where lower sensitivity is desired, metals can also be used to form the backing layer such as, for example and not meant to be limiting, indium, tin, and alloys of indium.

In another aspect, a lens layer can also be used. For example, a lens that is substantially acoustically matched to water can be used. Such a lens can have a speed of sound either higher or lower than that of water, but sufficiently different from water so that a practical curvature can be realized to achieve a desired amount of focusing. An exemplary lens material that can be used is polymethylpentene or TPX. This thermoplastic has an acoustic impedance of 1.8 MR and a longitudinal velocity of 2200 m/s. A convex lens (one with a speed of sound lower than water) can also be used.

TPX is lossy compared to some other alternatives (5.7 dB/mm at 30 MHz), but provides an exceptionally good acoustic match to water and tissue. The primary challenge in using TPX is that it is very difficult to bond to other layers of the ultrasonic transducer stack. For example, Rexolite (a thermo set cross linked polystyrene) has a lower loss than TPX having a loss of only about 1.1 dB/mm at 30 MHz, but has an acoustic impedance of 2.6 MR. Rexolite can be used where sensitivity is at a premium, and multiple reflections can be tolerated. By keeping the lens thin and the F-Number toward the higher end of the usual range, which is typically between about 2.5-3, the lossiness can be mitigated.

In various aspects, an exemplary at least one ¼ wavelength wave matching layer is used in the ultrasonic transducer stack. Conventionally, such ¼ wavelength matching layers are also known simply as "matching layers." It will be noted that the term "matching layer" is used throughout the description of the present invention and has the same meaning as ¼ wave or wavelength matching layer. The ¼ wave matching layer influences both sensitivity and bandwidth.

At high frequencies, matching layers can be on the order of between about 5.0 um to over 50.0 μm thick, and there is typically a low tolerance for intermediate adhesive layers. For example, a layer of more than 500 nm can be detrimental to the design, and anything over 1500 mm can substantially negate the effect of the stack. As will be clear to one skilled in the art, for a ¼ wavelength layer, the thickness depends on the desired transmit frequency and the speed of sound in the layer. One of skill in the art could thus readily determine the appropriate thickness for a ¼ wavelength for a matching layer comprising heavy and light particles through routine testing for the speed of sound of the composite and knowledge of the desired design frequency.

In one embodiment of the present invention, the exemplary lens layer comprises TPX that is connected to a cyanoacrylate matching layer, which has an acoustic impedance of approximately 3 MR. As described herein, the cyanoacrylate matching layer is bonded to the TPX lens layer for attachment to other layers of the stack.

In one exemplary embodiment, an approximately 10 MR matching layer is overlaid on a matching layer having an impedance between about 4.5-5 MR to enhance the bandwidth and maintain excellent sensitivity. This can exemplarily be accomplished using two layers of tungsten doped epoxy that are sanded to a desired thickness using a vacuum sander. In a further aspect, the lower impedance layer can also be doped with SiC nano-particles to prevent settling of the tungsten powder during curing.

As noted above, another matching layer can be the cyanoacrylate (CA) layer deposited thereon the TPX lens. The CA matching layer, bonded to the lens layer, can be bonded with a layer of epoxy to the lower impedance matching layer, which is located in the stack underneath the bottom surface of the CA layer. In one aspect, the elevational thickness of the epoxy layer is about 5 μm thickness or less. Due to the acoustic similarity of the epoxy to the CA, at a thickness of a few microns (<5 μm at 20 MHz) this layer is not significant to the performance of the stack. In one aspect, the epoxy can be, for example and not meant to be limiting, Epotek 301 epoxy. In another aspect, a rubber toughened CA (such as Loctite Black Max) can be used which can have a slightly lower acoustic impedance.

In alternative embodiments of the present invention, a matching layer for an ultrasonic transducer stack comprising a plurality of layers can comprise a composite material having a matrix material loaded with a plurality of micron-sized and nano-sized particles. In one aspect, the composite material forms the matching layer of the ultrasonic transducer stack. The matching layer can be a ¼ acoustic wavelength matching layer.

The particles can be of varying dimension within the respective nano and micron size domains. In one preferred embodiment, the loaded particles have a largest lengthwise or elongate dimension that is less than the thickness of the matching layer. For example, the micron-sized particles have a largest lengthwise dimension that is about 5 μm and the nano-sized particles have a largest lengthwise dimension that is about 800 nm wherein the matching layer thickness is larger than 5 μm. One skilled in the art will appreciate that the selected particles are as small as possible without making it impossible to get to the desired acoustic impedance. Nominally, in a matching layer, attenuation should be kept to a minimum, and the particle size is much smaller than a wave length. For example, a 5 μm particle in a 16.5 μm quarter wave layer is approximately ⅓ of a wave length.

In one aspect, the micron-sized and nano-sized particles can comprise a high density metal. For example, the micron-sized and nano-sized particles can comprise tungsten, gold, platinum or a mixture thereof. Alternatively, high density ceramics, such as, for example, PZT, can be used if a non-conductive layer is desired.

In a further aspect, the matrix material can be a polymer. In one non-limiting example, the polymer forming the matrix is an epoxy. For example, the epoxy can be a low viscosity, room temperature cure epoxy with a Tg above the maximum operating temperature of the transducer. Some non-limiting epoxy examples include Epotek® 301 and 302 (Epotek, Billerica, Mass.), Cotronics Duralco® 4461 (Cotronics, Brooklyn, N.Y.), West Systems Epoxies (West Systems, Bay City, Mich.) and various Araldite® Epoxy combinations. Alternatively, the matching layer can also be a thermoplastic such as polymethylmethacrylate (PMMA), e.g., acrylic, plexiglas, Lucite, or polycarbonate (PC), e.g., Lexan.

In one exemplary aspect, the micron-sized and nano-sized particles can be loaded in the matrix material in a ratio of between about 5:1 and about 1:5 parts micron-sized particles to nano-sized particles by weight. For example, the micron-sized and nano-sized particles can be loaded in the matrix material in a ratio of between about 1:1 part micron-sized particles to nano-sized particles by weight. In another aspect, as the desired acoustic impedance increases, the desired percentage of large particles can increase. For example, if a 10 MR matching layer is desired, a 1:1 ratio can be used. In another example, for a 12 MR layer, a ratio of 2:1 or 3:1 micro:nano can be used.

In some exemplary aspects, the nano-sized particles and micron-sized particles of the matching layer comprise between about 10% and about 35% of the composite material on a volume basis. In other examples, the nano-sized particles and micron-sized particles can comprise between about 25% and about 30% of the composite material on a volume basis. In one preferred embodiment, the nano-sized particles and micron-sized particles comprise about 25% of the composite material on a volume basis.

The matching layer having nano and micro particles can be designed with a desired acoustic impedance. For example, the acoustic impedance of the matching layer can be formed to be between about 7.0 MegaRayles (MR) and 14.0 MegaRayles (MR). In one preferred aspect, the acoustic impedance of the matching layer is about 10 MR.

In various aspects, the matching layer can also vary in thickness. As one skilled in the art will appreciate, the thickness to achieve a ¼ wavelength matching layer will vary with the speed of sound in the matching layer and the frequency of the ultrasound passing through the matching layer. Thus, one of skill in the art could readily determine the appropriate thickness of a matching layer based on the teachings herein in combination with any desired ultrasound transmit frequency, including frequencies at and above 20 MHz. In other exemplary aspects, the speed of sound in the matching layer can be between about 1000 meters per second (m/s) and 3000 m/s. Further, the elevational thickness of a matching layer can be between about 4 µm and 30 µm.

In one embodiment, a process for producing the nano/micron particle matching layer comprises providing a matrix material, a plurality of micron-sized particles and a plurality of nano-sized particles. The matrix material is loaded with a plurality of the micron-sized particles and a plurality of the nano-sized particles to form a composite material and the formed composite material is used to produce the matching layer of an ultrasonic transducer stack. In one aspect, the micron-sized particles and the nano-sized particles can comprise the same base material. Of course, it is contemplated that the micron-sized particles and the nano-sized particles can also be comprised of different base materials.

As shown in FIG. 1, the nano/micro particle matching layer can be used as a matching layer in an exemplified ultrasonic transducer stack 100 having a plurality of layers. As illustrated, the exemplary ultrasound stack 100 comprises a plurality of layers, each layer having a top surface and an opposed bottom surface. The plurality of layers includes a piezoelectric layer 102 and at least one matching layer. Of course, multiple matching layers (108, 110, and 112) can be used in the transducer stack 100. The matching layer 108 comprises the ¼ wavelength acoustic matching layer described above.

In some exemplary embodiments, the piezoelectric layer can generate ultrasound at a center frequency of at least about 20 megahertz (MHz) for transmission through the first matching layer. Such high transmit center frequencies may be particularly desirable for imaging small animals, including rats. Thus, in one exemplary aspect, the piezoelectric layer can generate ultrasound at a center frequency of at least about 20 MHz, 25 MHz, 30 MHz, 35 MHz, 40 MHz, 45 MHz, 50 MHz, 55 MHz, 60 MHz, 65 MHz, 70 MHz or higher for transmission through the first matching layer.

In another aspect, the piezoelectric layer can have an acoustic impedance of 20 MR or greater. As noted above, one exemplary type of piezoelectric layer that can be used comprises lithium niobate, which has an impedance of about 34 MR. In another example, the piezoelectric layer can comprise PZT, which has an impedance of about 33-35 MR.

Of course, in addition to the nano/micro matching layer described herein, other matching layers can be used. One exemplary matching layer of an ultrasonic transducer stack having a plurality of layers comprises a composite material comprising a matrix material loaded with a plurality of first heavy particles and a plurality of second light particles. It should be noted, however, that the light and heavy particles are not limited in size in this embodiment. Thus, the matching layer comprising the light and heavy particles can comprise a mixture of nano and micro particles. For example, the light particles can be micro sized or nano sized and the heavy particles can be micro sized or nano sized, any combination of which can be added to the matrix material.

The matching layer having heavy and light particles can comprise a ¼ acoustic wavelength matching layer. In some non-limiting examples, the light particles have a mass density of about 4.0 grams per cubic centimeter (g/cc) or lower and the heavy particles have a mass density of greater than about 4.0 g/cc. For example, the light particles can have a mass density of between about 2.5 g/cc and about 4.0 g/cc. The heavy particles can have a mass density of, for examples, 10.0 g/cc or more.

For example, the first heavy particles can comprise micron-sized or nano-sized particles selected from the group consisting of tungsten particles and lead zirconate titrate particles or a mixture thereof. In a further example, the second light particles comprise micron-sized or nano-sized particles selected from the group consisting of silicon carbite particles and alumina particles or a mixture thereof. Further, the density of the second light particles can be between about 100%-200% of the density of the final composite of the heavy particles and the matrix.

As described above, the heavy and light particles can vary in size. In various aspects, the heavy or light particles can be less than 1 micron. In a preferred embodiment, the loaded particles have a largest lengthwise or elongate dimension that is less than $\frac{1}{50}^{th}$ of a wave length in the matching layer which they comprise. The heavy and light particles can be loaded in the matrix material, which can comprise a polymer such as, for example, an epoxy. In one example, the loaded plurality of particles can comprise at least about 11.0% of the composite material by volume. For example, the plurality of particles can comprise between about 11.0% and about 20.0% of the composite material by volume. In a preferred embodiment, about 5.5% of the composite material by volume comprises a plurality of nano-sized heavy particles and about 5.5% of the composite material by volume comprises a plurality of nano-sized light particles. In this preferred embodiment, as in other exemplary embodiments, the heavy particles can be tungsten particles, PZT particles, gold particles, or platinum particles and the light particles can be silicon carbite particles or alumina particles.

The acoustic impedance of the matching layer comprising heavy and light particles can vary. For example, the acoustic impedance of this layer can be between about 3.0 MegaRayles and 7.0 MegaRayles. In one exemplary embodiment, the acoustic impedance is about 4.5 MR.

The thickness of the matching layer can also vary. One skilled in the art could thus readily determine the appropriate thickness for a ¼ wavelength for a matching layer comprising heavy and light particles through routine testing for the speed of sound and knowledge of the desired transmit frequency. In one example, the matching layer can have a speed of sound of between about 1500 m/s and about 4500 m/s. In other examples, the speed of sound in the matching layer is between about 1800 m/s and about 2500 m/s. In one preferred embodiment, the speed of sound in the matching layer is about 2100 m/s. In various aspects, it is contemplated that the thickness of the exemplified matching layer comprising heavy and light particles can be between about 4.0 microns and 30 microns. For example, for an exemplary 20 MHz center frequency transducer, for a 25 MHz design frequency, comprising an exemplary mix of about 5.5% of the composite material by volume of nano-sized first heavy particles and about 5.5% of the composite material by volume of nano-sized second light particles, the matching layer is about 22.0 microns thick in the elevational dimension of the ultrasonic transducer stack.

In one embodiment of the present invention, a process for producing the light/heavy matching layer comprises providing a matrix material, a plurality of first heavy particles and a plurality of second light particles. In this aspect, the matrix material is loaded with a plurality of the first heavy particles and a plurality of the second light particles to form a composite material that is used as a matching layer of an ultrasonic transducer stack.

An ultrasound transducer stack can comprise a matching layer comprising light and heavy particles as described above. This matching layer can comprise a lower impedance matching layer of a transducer stack that also comprises a higher impedance matching layer. In this aspect, the higher impedance matching layer comprises nano and micro particles of similar weight and or material as the lower impedance matching layer.

Thus, an exemplary stack 100 can comprise a plurality of layers, each layer having a top surface and an opposed bottom surface. The plurality of layers can include a piezoelectric layer 102 and at least one matching layer. A matching layer 110 can comprise a composite material comprising a matrix material loaded with a plurality of first heavy particles and a plurality of second light particles, wherein the bottom surface of the matching layer 110 overlies the top surface of the piezoelectric layer 102. The ultrasound transducer stack 100 can further comprise a matching layer 108 having a higher impedance than the impedance of the matching layer 110, the matching layer 108 being positioned between the top surface of the piezoelectric layer 102 and the bottom surface of the matching layer 110.

The piezoelectric layer can generate ultrasound at a center frequency of at least about 20 megahertz (MHz) for transmission through one or more matching layer. For example, the piezoelectric layer can generate ultrasound at a center frequency of at least about 25 MHz, 30 MHz, 35 MHz, 40 MHz, 45 MHz, 50 MHz, 55 MHz, 60 MHz, 65 MHz, 70 MHz or higher for transmission through one or more matching layer. The ultrasound can be transmitted through the matching layer 108 and then through the matching layer 110.

Also provided herein is a backing layer 104 of an ultrasonic transducer stack 100 having a plurality of layers. The backing layer can comprise a composite material having a matrix material loaded with a plurality of micron-sized and nano-sized particles. Also provided is a backing layer 104 of an ultrasonic transducer stack 100 comprising a composite material having a matrix material loaded with a plurality of first heavy particles and a plurality of second light particles.

EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

EXAMPLE 1

Fabrication of an Exemplary LiNb 20-25 MHz Transducer Stack with a TPX Lens

Figure 5A:
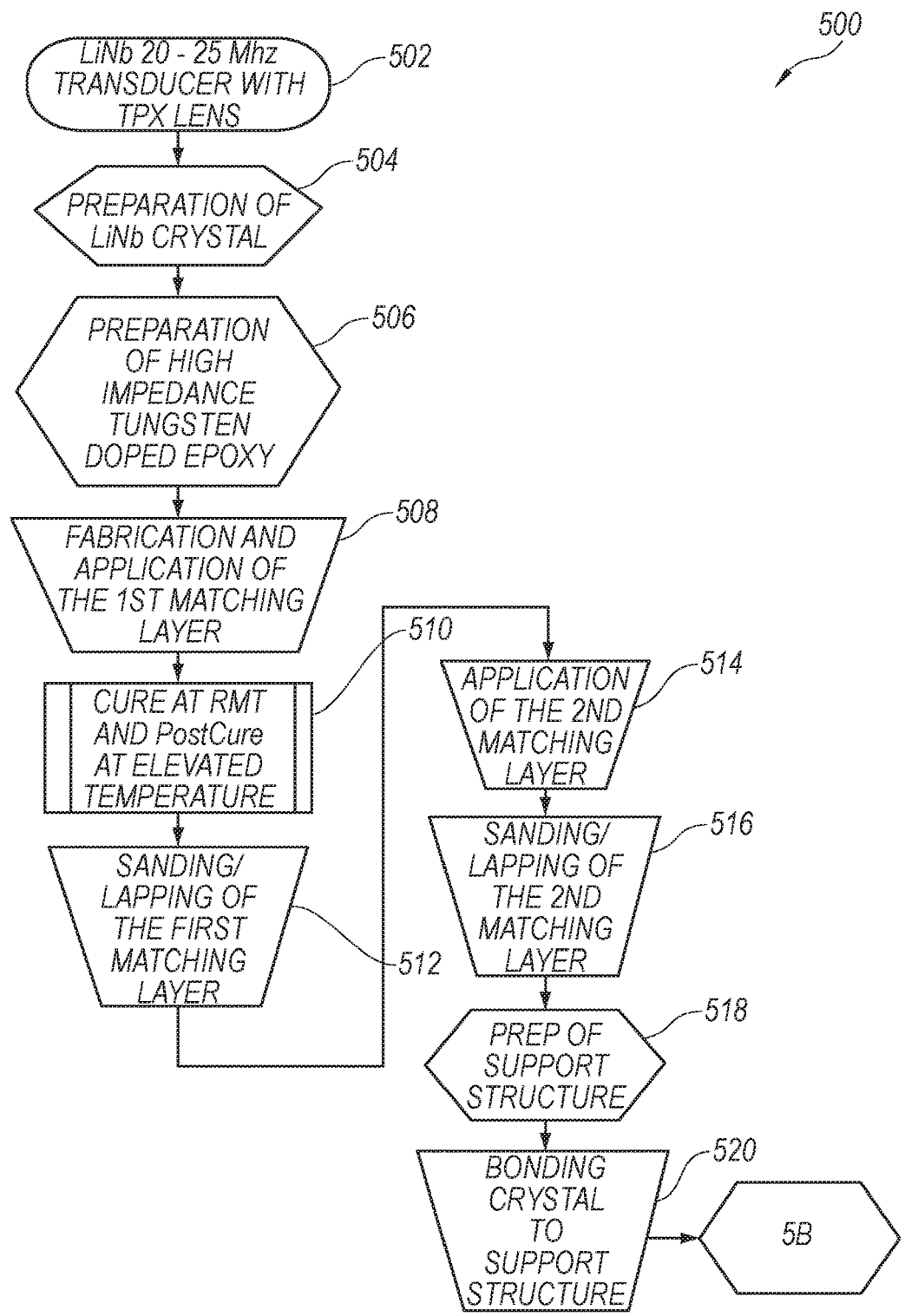
FIGS. 5A-5C are block diagrams illustrating exemplary methods of fabricating an exemplary transducer stack.
Figure 5B:
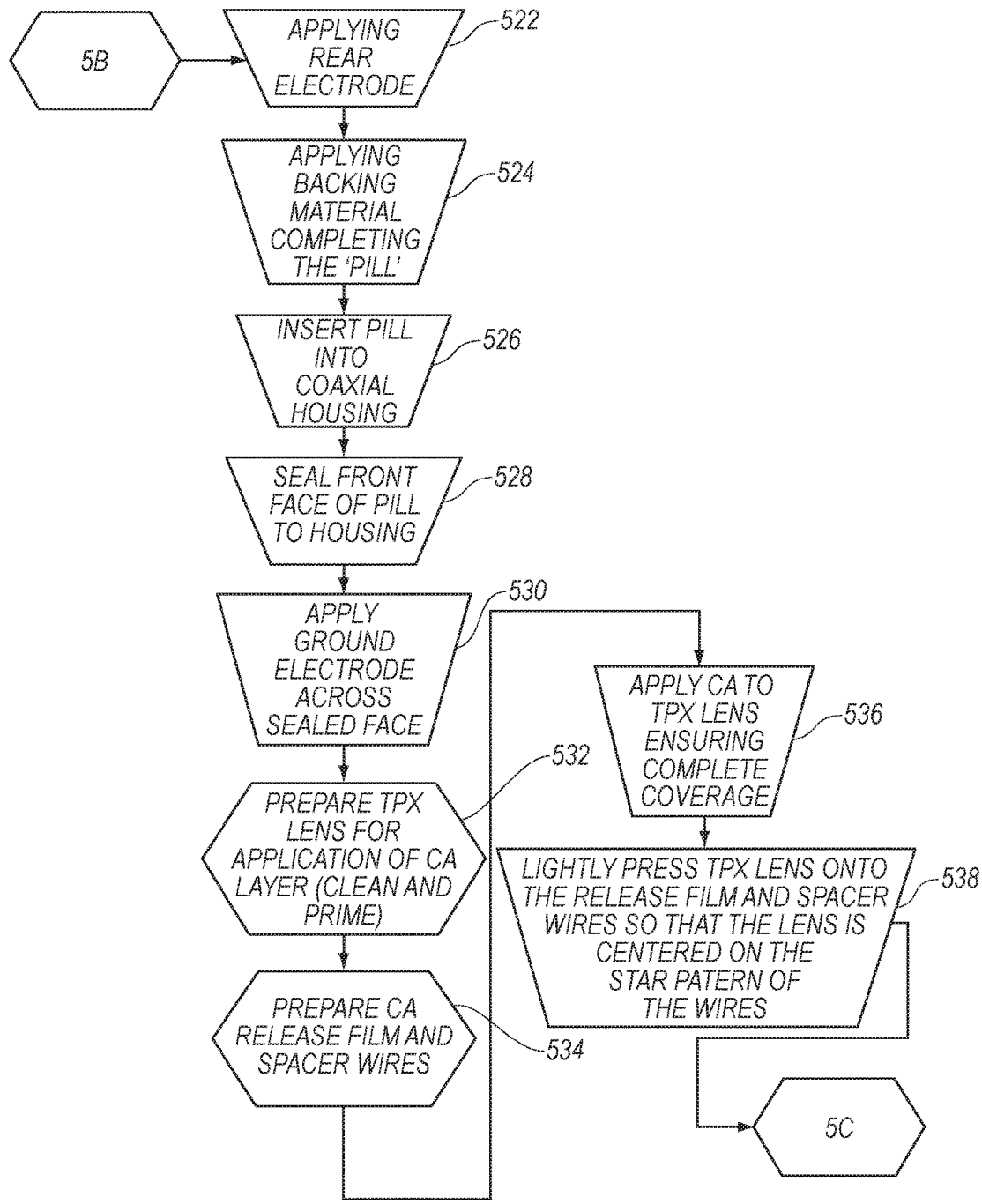
Figure 5C:
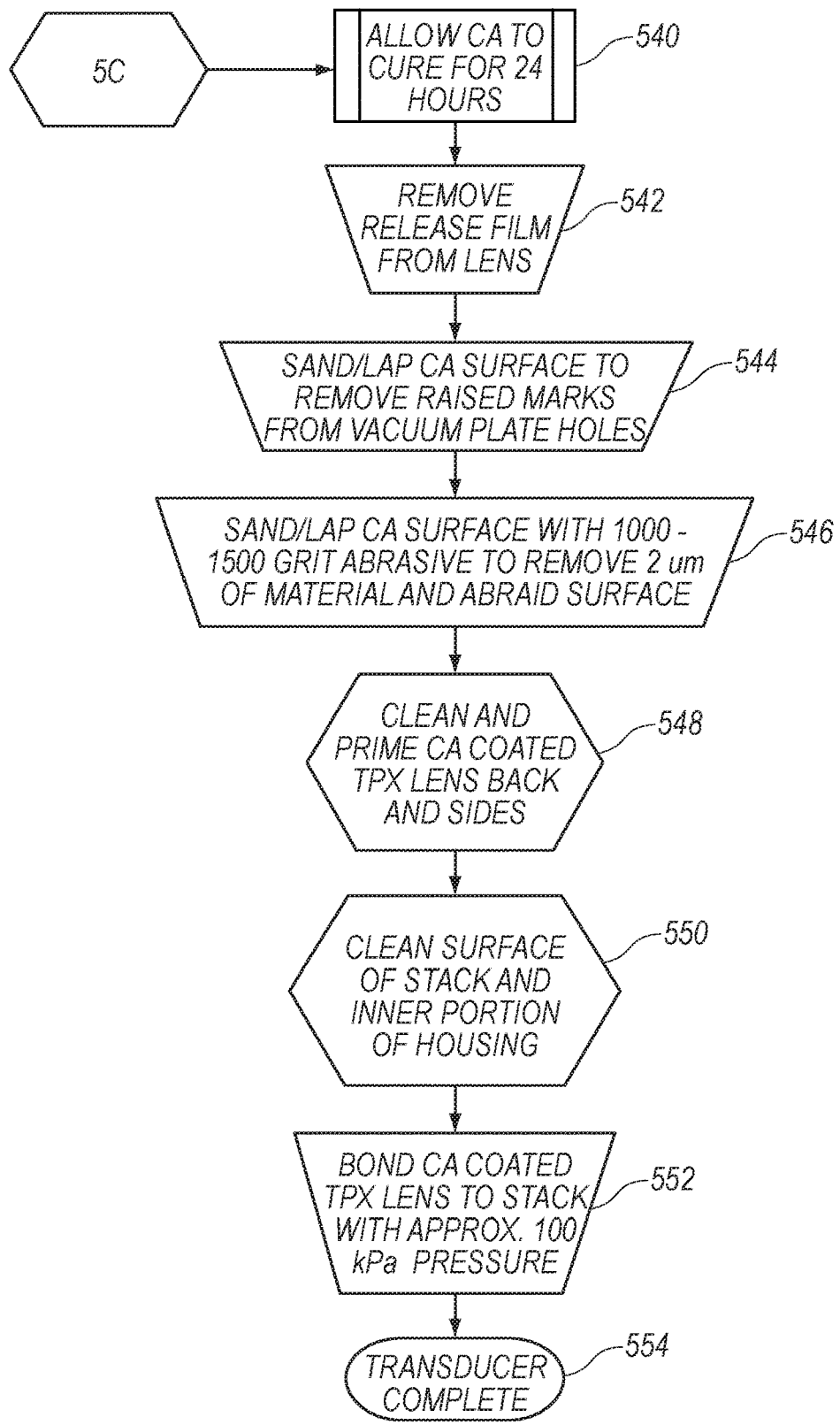

FIG. 5 is a block diagram showing an exemplary method of fabricating an exemplary LiNb 20-25 MHz transducer with a TPX lens. The fabrication process is described below in three exemplary sections. First, the fabrication of matching layers and piezoelectric layer to form a stack is described. Second, the fabrication of the lens layer and a cyanoacrylate matching layer is described. Finally, bonding of the lens and cyanoacrylate layer to the transducer stack is described.

Matching Layer and Piezoelectric Layer Fabrication

A LiNb Crystal is prepared for the piezoelectric layer as shown in block 504. A 36 degree Y-Cut LiNb crystal is lapped to a thickness of 0.4 lambda of the desired center frequency to compensate for mass loading. The crystal is plated with 3000 A of gold using a suitable means such as E-Beam deposition or Sputtering. As one skilled in the art will recognize, typically a thin layer of Cr or Ni can be used to improve adhesion of the gold layer. The gold side of the LiNb crystal is cleaned with Acetone. After cleaning, the crystal is placed in a clean place until further handling.

A nano-particle and micro-particle loaded epoxy is prepared for ¼ wave matching layers. A high impedance matching layer, having an impedance above about 8 MR is prepared in block 506. Creating a loaded epoxy composite with acoustic impedance over 8 MR is typically limited by the maximum volumetric ratio of powder that can be wetted by the epoxy. Achieving volumetric ratios of over 20% with particles small enough to be compatible with a 25 MHz design is challenging due to the large surface area to volume ratio of fine powders. With a 20% volumetric limitation and using tungsten powder, it is difficult to create composites with acoustic impedances over about 8-9 MR. See, e.g., Martha G. Grewe, T. R. Gururaha, Thomas R. Shrout, and Robert E. Newnham, "Acoustic Properties of Particle/Polymer Composites for Ultrasonic Transducer Backing Applications," IEEE Trans. on Ultrasonics, Ferroelectrics and Frequency Control, Vol. 37, No. 6, November 1990.

The use of a low viscosity epoxy (less than 1000 cps is preferred) allows for the greatest volumetric ratio of powder to be added to the epoxy before the mixture becomes too dry to use. An example of such an epoxy, known in the art, is Epotek 301. See, e.g., Haifeng Wang, Tim Ritter, Wenwu Cao, and K. Kirk Shung, "Passive Materials for High Frequency Ultrasound Transducers", SPIE Conf. on Ultrasonic Transducer Engineering, San Diego, Calif., February 1999, SPIE Vol. 3664. The epoxy is mixed completely before addition of any powders.

To create an exemplary 10 MegaRayles matching layer, a volumetric ratio of 25% powder in an epoxy matrix is used. To achieve this volumetric ratio, relatively large 5 µm particles are used. However, such large particles are not compatible with the frequency of the transducer, as they would allow for only 3 grains through the thickness of a matching layer. A sub-micron tungsten (W) powder mixed with the 5 µm powder to a ratio of 1:1 is also used. This is effective over a range of at least 1:6 to 2:1 by weight. The upper limit of density that can be achieved in a powder loaded epoxy is limited by the ability to wet the surface of all the powder particles. As the particle size increases, the ratio of the volume of the powdered material to the surface area increases linearly. Thus, as the powder particle diameter increases, the volumetric ratio of powder to epoxy that can be sufficiently wetted to result in a void free mixture increases. However, as the particle size increases, issues arise with settling and the increasingly significant interaction of individual particles with the wavelength of the ultrasonic energy.

To reduce attenuation in a matching layer and for predictable acoustic impedance of the matrix and powder as a compost material, the particle diameter can be small compared to the wavelength of the matrix (epoxy). For making a ¼ wave matching layer, the particle size can be sufficiently small that the composite contains at least 15 or more particles through its thickness.

The exemplified use of a mixture of nano-particles with larger particles allows for high density loaded powders with both high volumetric fractions of the loading powder and excellent control over settling. Settling is controlled by adjusting the amount of nano-particles to control the viscosity and thixotropic index of the resulting paste. In addition to the advantages gained in the upper limit to the volumetric fraction attainable and the reduction of settling of larger particles, the nano-particles also provide that at any given cross section, the ¼ wave layer (16.5 µm thick at 25 MHz for example) has a high number of particles and an even spatial distribution of powder particles (i.e. there are no large areas of epoxy between large particles as would be the case with just large particles).

A mixture of large and small particles is preferred. The use of only the nano-particles results in an upper limit of less than 20% by volume being possible, while the exclusive use of 5.0 µm particles or even 2.0 or 3.0 µm particles results in a highly attenuative matching layer with a poorly defined acoustic impedance due to large spaces between particles compared to the wave length. An exemplary W doped Epoxy preparation comprises a mixed batch of 3:1 vol./vol. Epotek 301 epoxy to 50%:50% 5 µm: <1 µm tungsten powder. This is a highly thixotropic paste and is an 85% by weight tungsten mixture with a density of 5.7 g/cc and a volumetric fraction of 25% tungsten. Due to the small size of the nano-sized particles it has up to 50 particles through its thickness. For example, the mixture can be weighed out as follows: 0.5 g of mixed 301 epoxy (0.1 g of hardener and 0.4 g of resin); 1.5 g of <1 µm W powder; 1.5 g of 5 µm W powder.

A medium acoustic impedance matching layer, having an impedance between about 3.5 MR to 6 MR is fabricated as shown in block 514 by mixing lightweight particles with heavy particles. The creation of medium acoustic impedance matching layers can use high volumetric fractions of a single light particle to achieve mid and upper impedances in this range. However, using a single material, with a sufficiently small particle size to create medium acoustic impedance typically requires a difficult search for an appropriate density material available in a suitable powder grain size. High volumetric fractions make mixing, degassing, and spreading/application very difficult due to high viscosity and highly thixotropic pastes being created, which leads to manufacturing issues. However, since the volumetric fraction of powder is typically kept above 11% to keep attenuation low, often a compromise must be made between achieving the ideal acoustic impedance and ideal physical properties, or a new material must be sought and the process begun again.

Thus, using light and heavy dopants together, a solution is possible that decouples the problem of achieving the desired acoustic impedance from the issues of viscosity, wetting, and thixotropic index. A heavy material is mixed to a volumetric fraction resulting in the desired acoustic impedance, then light nano-particles are added until a desirable viscosity and thixotropic index are achieved (i.e., a paste that is easily wetted, but will not flow all over or settle.) In one example, a commercially available light weight nano particle of SiC may be used as the light weight particle. Several such particles can be used including but not limited to SiC p=3.2 g/cc and alumina p=3.9 g/cc to decouple the problem of wetting, viscosity, and thixotropic index, from that of achieving a given acoustic impedance.

In this way, the acoustic impedance of the matching layer is controlled almost exclusively by the volumetric fraction of the heavy powder, which would have significant settling issues at that fraction. However, the viscosity and consistency of the composite mixture and settling is controlled almost exclusively by the light weight powder. In this aspect, the light weight powder is selected so that its density is within between about 100% to 200% of the density of the desired composite density of the heavy powder-epoxy mixture.

For example, in an exemplary 25 MHz 4.5 MR matching layer, a 5.5% volumetric fraction of nano-particles of tungsten powder is used in a suitable room temperature cure low viscosity epoxy to achieve an acoustic impedance of between about 4.5 MR-5 MR. SiC nano-particles are then added to achieve an exemplified 11% volumetric fraction.

This exemplified mixture is easy to work with, wets very well, and does not settle appreciably over a 24 hour cure period during which the epoxy sets. Before addition of the SiC particles, the mixture settles out completely in seconds, however, after the addition of the SiC, the mixture becomes thixotropic, and does not settle. The addition of SiC particles minimally changes the acoustic impedance, but significantly changes the viscosity and eliminates settling of the mixture. Any desired acoustic impedance can be achieved in the medium range while maintaining a desirable working property without settling, and without needing extremely high volumetric fractions using two readily obtainable powdered materials. Also due to the size of the nano-particles, attenuation and scattering are kept to a minimum, making this an exceptional matching layer.

The W-Doped epoxy can be added to the stack as shown in block 508. Application of the matching layers requires careful attention, as air pockets in the matching layer can generally result in a malfunctioning stack. Air pockets near the interface of the piezoelectric crystal and the powder loaded epoxy can be detrimental.

To prevent air pockets the loaded epoxy is spread evenly and air pockets are forced to the surface of the mixture. Generally, the thixotropic pastes used to make matching layers are difficult to 'flow' onto a part and normally require agitation to flow like a liquid. Thus, a vibrating manipulator (for example, an engraver with a piece of 22 gauge wire attached to it) can be used to spread the paste over the surface of the crystal so that it flows and wets the entire surface. Further, the vibration encourages air pockets to rise to the surface of the paste, where they can be sanded away. This allows the use of highly thixotropic pastes that do not settle after they have been spread as desired.

In one example, under the microscope, an engraver tip modified with 22 gauge hard temper copper wire L-Shaped tip is used to move the thixotropic paste smoothly over the surface for good wetting and promotion of the rising of air pockets to the surface. Typically, the engraver tip is used over the entire surface of the aperture and is set to a low amplitude high frequency setting (about 7,200 spm). In one aspect, the surface of the LiNb crystal is covered leaving a small part of the rim (about 0.25 mm) uncovered around the edge so that it can be used for a ground later. If epoxy is placed on the rim, it cannot be cleaned effectively without removing the whole batch off the face of the transducer.

The epoxy is allowed to cure at room temperature and post cure at an elevated temperature as shown in block 510. Room temperature cure epoxies are used so that significant shrinkage of the layers, which can cause warping of the piezoelectric crystal, does not occur. A high Tg is preferred, so an epoxy is selected that is compatible with an elevated temperature post cure in an oven. The epoxy is allowed to cure at room temperature for about 18 hours or more (24 hours is preferred). Further, the cured epoxy is post cured in incubator for about 3 or more hours at 65 degrees C.

The first matching layer is sanded and/or lapped as shown in block 510. Excess material is removed to achieve the ¼ wave matching layers. Several methods (such as lapping or sanding, etc.) can be used to remove excess material leaving a ¼ wave thickness matching layer. A sanding system is used to sand the $1^{st}$ matching layer to a thickness of lambda/4 with c=1600 m/s (for the 25 MHz version this is 16-17 µm thick). Care is used to mount and measure the samples, as tolerances for an exemplary 20 MHz device for a design frequency of about 25 MHz are in the 2-3 µm range, i.e., 16.5 µm+2 µm/−1 µm.

A second lower impedance layer is fabricated and applied as shown in block 514. After completing a first matching layer, a second medium acoustic impedance paste is applied to the first layer and the process of spreading, curing, and material removal is repeated to create the second ¼ wave layer. A batch is mixed as follows: W powder doped epoxy using a 17:1 vol./vol. or (51% W by weight) mixture of Epotek 301 and <1 µm Tungsten powder. 50% of the mass of the mixture in <1 µm SiC powder is added and mixed until a smooth paste is achieved. Any lumps in the paste can be removed by mixing lightly in a mortar and pestle. The mixture may be weighted out as follows: 0.5 g of mixed 301 epoxy; 0.52 g of <1 µm W powder; 0.2 g of <1 µm SiC powder. The second layer is applied as with the 1st, using the L-shaped tip in the engraver for even spreading of the paste, and for good wetting. The mixture is allowed to cure at room temperature for about 18-24 hours, then post cured at 65 degrees for about 3 hours or more.

The second matching layer is sanded and/or lapped as shown in block 516. The material is sanded to a thickness of Lambda/4 using c=2100 m/s, i.e., for the 25 MHz design frequency example this thickness is about 18-19 µm thick+/−1 µm).

The support structure for the stack is prepared and the crystal is bonded to the support structure as shown in blocks 518 and 520. In one aspect, the stack is positioned in a housing. A Ultem 1000 (polyetherimide) insert can be used having an ID matching the desired transducer aperture and height and OD matching the specifications of the desired Ti transducer housing so that the top of the insert is about 1.5 mm below the rim of the Ti housing. The front face of the insert is cleaned and inspected so that it is clean and free of burrs or flashing. For example, the insert can be cleaned with the ultrasonic cleaner and detergent initially and can be cleaned just before use with isopropyl alcohol.

A small quantity of a suitable low temp cure medium viscosity epoxy (e.g., Loctite E-20 HP) is prepared and is applied to the cleansed front face of the insert in a very thin coat using a sponge tipped swab. The epoxy is not applied so heavily as to form a meniscus across the wall thickness of the insert. In operation, the crystal is placed, with the stack side up, onto the epoxy covered face of the insert and is centered on the insert. In one example, the lithium niobate crystal is applied to the insert by using a vacuum pick-up tool. A small amount of force is applied to push the crystal onto the face of the insert, which causes the epoxy to flow toward the edges of the underlying insert. The centered crystal is placed into an incubator for curing at about 40 degrees C. for about 3 hours.

After curing, the insert/crystal assembly is inspected to ensure that the crystal is centered and completely adhered to the insert. Subsequently, the periphery of the insert/crystal assembly is cleaned. The non-increased diameter of the Ultem insert is checked by sliding the part into an exemplary housing.

At this stage, one skilled in the art will appreciate that the acoustic stack can be housed onto a suitable support structure and a rear electrode and suitably attenuating backing material can be applied as shown in blocks 522 and 524. These functions can be combined by using conductive epoxy as a backing layer.

In one example, the exemplified insert/crystal assembly is normally placed in a clean smooth work surface crystal layer down. The back cavity is filled with Ablebond 16-1 silver conductive epoxy. The cavity is filled by first placing a dollop of epoxy in the center of the cavity using an epoxy syringe and applicator tip. The epoxy is applied to the entire back face of the crystal making sure not to allow any air pockets to be trapped in the backing material. The epoxy syringe is used to continue filling with the tip of the applicator below the surface of the epoxy so that no air pockets are created in the epoxy when filling. The cavity is filled until the conductive epoxy is about 0.5 mm below the rim of the insert.

The backed stack, called a "pill," can now be housed in a suitable housing depending on the application that the device is intended for, taking into consideration, weight budgets, temperature, and RF shielding, etc. and is sealed as shown in blocks 526 and 528.

The pill is placed onto the Housing fixture with the uncured epoxy up. Several small dots of Loctite E-20 HP are applied to the back rim of the pill such that the dots do not flow together. Next, a completed housing is laid over the pill until the pill makes contact with the back of the housing. Subsequently, the fixture clamp is placed over the housing to hold it in place, and allowed to cure at room temperature for about 18 hours or more. The assembly is then placed into an incubator at 65 degrees for about 3 hours for post curing. Typically, the face of the pill is oriented parallel to the floor and pointing down to help prevent the backing layer from flowing inside the housing.

Next, a sealing layer can be applied. In this example, when the epoxy is fully cured, a bead of epoxy is applied around the perimeter of the crystal so that a continuous smooth surface exists between the crystal and the Ti housing. Here, a very small amount of Epotek 301 epoxy is placed around the perimeter of the LiNb crystal and the inside diameter of the housing. The surface of the crystal is about 1.25 mm below chamfer on the Ti housing in order to desirably achieve a negative meniscus of epoxy between the crystal and the Ti housing. Both the crystal and the Ti are clean and free of epoxy on their surfaces so that gold can be sputtered onto both surfaces. In operation, a high magnification (about 20 times and preferably more) is used to place the epoxy bead. In one example, the epoxy can be applied at three locations around the perimeter and allowed to run around the perimeter using gravity and capillary action. In a further example, a piece of fine gauge wire (26 gauge or so) can be attached to the end of a sharp Q-tip to improve control to help the glue to flow around the entire perimeter. The resultant construct is allowed to cure at room temperature for about 12-18 hours. The sealing procedure can be repeated and the construct is allowed to cure at room temp for about 18 hours then is incubated at 65 degrees for a post cure of about 3 hours. After the epoxy has cured, the rim of the Ti housing is inspected for epoxy. Any epoxy found on the rim is removed.

As one will appreciate, a ground connection to a signal return path is made to the exposed gold rim of the acoustic stack as shown in block 530. Again, one skilled in the art will recognize several methods of attaching such an electrode including sputtering, conductive inks and epoxies, direct mechanical contact with a good conductor, etc.

In one example of the ultrasonic stack, the stack, as formed above, can then be bonded to a third low impedance matching layer and a lens. A well-matched lens is selected. As noted above, in one preferred embodiment, the lens is closely matched to water in terms of acoustic impedance to provide for a reduction of reverberation artifacts. Furthermore, the lens material can be low in attenuation and have a speed of sound sufficiently different from water so as to be able to create a focusing effect without extreme curvature. There are many exemplary materials that have been used to form the lens for ultrasonic transducers. Furthermore, many transducer designs make use of cured piezoelectric elements, or array structures as alternatives to lenses.

For the purposes of imaging rats, the reverb artifact is a significant concern in the design of a lens. While other materials exist that have lower loss at high frequency, or more refractive power, TPX was identified as a preferred lens material that has an acoustic match to water. TPX is a member of the polyolefin family and has a close acoustic impedance match to water and tissue compared to most plastics. TPX has an acoustic impedance of between about 1.78 MR to 1.85 MR. See, e.g., Alan R. Selfridge, "Approximate Material Properties in Isotropic Materials," IEE Trans. Sonics and Ultrasonics, Vol. SU-32, No. 3, May 1985. The impedance of water is Z=1.5 MR.

It is well known that TPX is difficult to bond with epoxies and most other adhesives. The most common use of TPX in industry is as a release film. That is, TPX is recognized as a material that most things will not stick to. While some surface preparation techniques can be used to enhance bond strength, in fact, even with adhesion promoters and primers, or coronal etching TPX is often not bondable in a demanding application and must be jointed either mechanically or heat sealed or welded. See, Timothy Ritter, K. Kirk Shung, Xuecang Geng, Pat Lopath, Richard Tutwiler, and Thomas Shrout," Proceedings of SPIE—Volume 3664 Medical Imaging 1999: Ultrasonic Transducer Engineering, K. Kirk Shung, Editor, June 1999, pp. 67-75.

The bondline between a lens and an acoustic stack in an imaging transducer can experience temperature swings of over 40 degrees Celsius in a few minutes, and rapid cooling routinely during use. In addition, it is constantly bombarded with ultrasonic energy. Weakness in bonding generally results in delamination and dead spots in the transducer. For this reason, high quality bond lines are desired for transducer construction.

For the exemplary high frequency ultrasonic transducers, the lens remains in contact with the stack at all times. Even a thin disbond can result in a dead spot in the transducer.

In one exemplified example, cyanoacrylate (CA) adhesive systems are bonded to the TPX lens. With the use of a suitable primer such as, for example and not meant to be limiting, Verik AC77, some toluene based primers, and the like, CA can form a robust bond to TPX. However, because of cyanoacrylate's curing characteristics being very sudden and dependent on substrate and environmental conditions, CA has not been used in transducer stacks. The glue can snap cure suddenly at the very thin bond lines used in making a high frequency ultrasonic stack. The addition of bondline spacers is often not used with CA adhesives as they cause instant curing of the material due to their large surface areas. CA cannot be powder loaded for the same reason, further making it an unlikely candidate for transducer manufacturing. Moreover, acoustic properties of CA have not been available in the literature, as the material cannot be cured in a thick enough section for standard testing. Furthermore, material properties that may be used to acoustically model CA have been unavailable for similar reasons.

Despite the lack of art and drawbacks noted in the art, CA can be cured over a narrow range of thickness. The range over which CA can be cured can be used for forming ¼ wave matching layers for frequencies from 5 MHz up to over 60 MHz. The acoustic properties of CA were determined by using it as a matching layer and were correlated to a model using PiezoCAD software based on the KLM model available from Sonic Concepts, Woodinville, Wash. USA. The results showed that CA can be used as a matching layer with acoustic impedance of between about 2.5 MR-2.8 MR.

One exemplary method to bond TPX to a ¼ wave matching system makes use of CA. The bond between the TPX layer and the CA layer was tested and results indicated that the interface between the CA layer and TPX layer is at least as strong as the TPX itself. However, for reasons stated above, it is not suitable for bonding directly to the stack, as the bond thickness cannot be controlled, and voids and misalignment are likely, which can ruin an almost complete transponder stack at the last stages of assembly.

In one exemplary process, a ¼ wave thick cured layer of CA is created on the back (flat side) of the TPX lens layer, and the formed construct is then bonded to the upper surface of the previously formed stack with a traditional epoxy. The epoxy bonds readily to the CA layer, and the CA layer, which is, in turn, bonded to the TPX lens layer. Thus the CA layer forms a ¼ wave matching layer from the top of the stack to the TPX lens layer. In the case of the exemplary stack, the top of the stack has an acoustic impedance of 4.5 MR, with the CA having Z=2.5-2.8, and the TPX lens layer Z=1.8. This yields a transducer with a −6 dB bandwidth of 85%-90% and a two way insertion loss of between approximately −41 dB to −42 dB at 25 MHz re1V/V.

In one example, a quantity of CA glue, such as, for example, Verik PR40, is coated onto the back of the TPX lens by means of an aluminum foil release layer and wire spacers as shown in blocks 534 and 536. In operation, the release film is placed onto a flat surface (preferably a vacuum plate so that the foil is flat). In one aspect, the aluminum foil is clean and free of oil and moisture. Wires are laid in a pattern onto the release film. In one aspect, the wires are positioned in a radial pattern so that the wires do not meet at their common vertex. These wires are used as spacers for the layer of CA. For the exemplary 25 MHz stack, a wire having a diameter of about 25 μm is used to provide form a CA layer having a resultant thickness about 23 μm-25 μm. This is slightly thicker than the desired ¼ wave thickness for CA, which would be between about 21 to 23 μm for a 25 MHz design frequency transducer. In this aspect, it is estimated that the longitudinal velocity in CA is between about 2100 m/s to 2200 m/s. The 1-3 μm surplus material is removed during a later abrasion process which also acts to prepare the surface of the CA layer to improve adhesion of the epoxy used to glue the lens layer having the adhered CA layer to the underlying stack.

In operation, the back face of the TPX lens layer is abraded with a suitable grit SiC sandpaper to improve the surface for adhesion and is treated with a suitable CA polyolefin primer, such as, for example, Verik AC77, toluene based primers, and the like, as shown in block 532. The back of the lens is then covered with a generous amount of CA so that substantially the entire surface is wetted as shown in block 536. CA will not cure quickly when allowed to form a relatively thick meniscus on the back of the lens, and so the generous amount of CA provides sufficient time to place the lens onto the prepared release film/wire arrangement.

Subsequently, the lens layer, with the applied CA, is placed onto the release film and pressed lightly so that the lens "sandwiches" the wires between the underlying release film and the lens layer as shown in block 538. After curing for about two hours, the lens and the attached release film is removed from the vacuum plate and the release film is peeled off the lens layer as shown in block 542. Next, the CA layer is allowed to cure for about 24 hours, as shown in block 540, at which time 1-3 μm of CA are then removed with SiC sand paper to abrade the surface of the newly formed CA layer in preparation for bonding to the stack as shown in block 544.

The composite formed lens layer/CA layer is bonded to the transducer stack as shown in blocks 548, 550 and 552. In one example, a suitable low viscosity RT cure epoxy, such as Epotek 301, with an acoustic impedance value close to that of the CA layer is used to glue the composite lens layer/CA layer to the underlying stack. In one aspect, the lens is held in place using a fixture to maintain pressure of at least about 100 kPa during curing of the epoxy. An extended post cure at an elevated temperature using an external heat source is used for curing epoxy at such a thin bondline, which ensures the production of a bondline of less than 5 μm, and preferably from 1 μm-3 μm. One would appreciate that, since the acoustic impedance of the epoxy is similar to that of the CA, there is little, if any, contribution to the stack by this bond layer.

The above exemplary methods can be used to create a transducer stack wherein the piezoelectric layer has a center frequency range of from about 5 MHz to about 60 MHz or higher. Such a transducer can be used to image small animals, including the rat, using high transmit frequencies (greater than or equal to 20 MHz).

EXAMPLE 2

General High Frequency Design for an Exemplified Broadband (85-95%-6 dB bandwidth) LiNb Transducer with TPX Lens Table 1 shows the different layers that make up an exemplary transducer stack. The stack design can be used for transducers with a center frequency from about 20 MHz to over 60 MHz.

The design center frequency $f_D$ is chosen to be higher than the desired operating center frequency of the device $f_O$ to compensate for mass loading which reduces the center frequency of a device. $f_D$ is the frequency that the device would operate at in air with no lens and air backing. For this exemplary design, $f_D$ is chosen to be approximately 1.15 to 1.25 times the desired center frequency of the final transducer. For example, for a 20 MHz device, one would choose $f_D$=~23-25 MHz for the purpose of the relationships shown in Table 1 below.

TABLE 1

TPX Lens
CA (cyanoacrylate) ¼ Wave Matching layer
Thickness = $\frac{c_L}{4f_D}$, where $c_L$ is the longitudinal velocity of the relevant layer
Thin layer of Low Viscosity RTC Epoxy
(Typical: Epotek 301, Duralco 4461)
¼ Wave Matching Layer of Moderate Impedance SiC nano-particles and Tungsten nano-particles doped Epoxy Thickness = $\frac{c_L}{4f_D}$ ¼ Wave Matching layer of High Impredance Tungsten
(5 μm particles mixed with tungsten nano-particles doped Epoxy)

Thickness = $\frac{c_L}{4f_D}$

Thickness = $k\frac{c_L}{f_D}$, where k = 0.4

Conductive Epoxy Backing with Z = 5 MR-7 MR

Throughout this application, various publications are referenced. The disclosures of these publications in their entireties are hereby incorporated by reference into this application in order to more fully describe the state of the art to which this invention pertains.

The foregoing detailed description has been given for understanding exemplary implementations of the invention only and no unnecessary limitations should be understood therefrom as modifications will be obvious to those skilled in the art without departing from the scope of the appended claims and their equivalents.

The preceding description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. The corresponding structures, materials, acts, and equivalents of all means or step plus function elements in the claims below are intended to include any structure, material, or acts for performing the functions in combination with other claimed elements as specifically claimed.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Accordingly, those who work in the art will recognize that many modifications and adaptations to the present invention are possible and can even be desirable in certain circumstances and are a part of the present invention. Other embodiments of the invention will be apparent to those skilled in the art from consideration of the specification and practice of the invention disclosed herein. Thus, the preceding description is provided as illustrative of the principles of the present invention and not in limitation thereof. It is intended that the specification and examples be considered as exemplary only, with a true scope and spirit of the invention being indicated by the following claims.

The invention claimed is:

1. An ultrasonic transducer stack, comprising:
   a plurality of layers comprising:
   a piezoelectric layer;
   at least one matching layer that comprises a first matching layer, which comprises cyanoacrylate; and
   a lens layer comprising TPX,
   wherein each layer of the plurality of layers has a top surface and an opposed bottom surface, wherein the first matching layer is connected to and underlies the bottom surface of the lens layer, and wherein the piezoelectric layer underlies the bottom surface of the matching layer.

2. The ultrasonic transducer stack of claim 1, wherein the first matching layer is about a ¼ acoustic wavelength matching layer.

3. The ultrasonic transducer stack of claim 2, wherein the acoustic impedance of the first matching layer is between about 2.0 MegaRayles (MR) to about 3.5 MegaRayles (MR).

4. The ultrasonic transducer stack of claim 2, wherein the acoustic impedance of the first matching layer is between about 2.5 MegaRayles (MR) to about 2.8 MegaRayles (MR).

5. The ultrasonic transducer stack of claim 2, wherein the acoustic impedance of the lens layer is about 1.8 MegaRayles (MR).

6. The ultrasonic transducer stack of claim 1, wherein the acoustic impedance of the lens is substantially the same as the acoustic impedance of water.

7. The ultrasonic transducer stack of claim 1, wherein the piezoelectric layer can generate ultrasound at a frequency of at least about 20 megahertz (MHz).

8. The ultrasonic transducer stack of claim 7, wherein the piezoelectric layer can generate ultrasound at a frequency of about 20 MHz, 25 MHz, 30 MHz, 35 MHz, 40 MHz, 45 MHz, 50 MHz, 55 MHz, 60 MHz, or higher for transmission through the first matching layer and then through the lens layer.

9. The ultrasonic transducer stack of claim 1, further comprising a second matching layer located between the top surface of the piezoelectric layer and the bottom surface of the first matching layer.

10. The ultrasonic transducer stack of claim 9, wherein the top surface of the second matching layer is bonded to the bottom surface of the first matching layer using a bonding material.

11. The ultrasonic transducer stack of claim 10, wherein the bonding material forms a bondline layer between the first matching layer and the second matching layer.

12. The ultrasonic transducer stack of claim 11, wherein the bondline layer has an elevational thickness of less than about 5 microns.

13. The ultrasonic transducer stack of claim 11, wherein the bondline layer has an elevational thickness of between about 1 micron to about 5 microns.

14. The ultrasonic transducer stack of claim 11, wherein the bondline layer has an elevational thickness of between about 1 micron to about 3 microns.

* * * * *